US012016850B2

(12) United States Patent
Pertile et al.

(10) Patent No.: US 12,016,850 B2
(45) Date of Patent: Jun. 25, 2024

(54) MODIFIED RELEASE PHARMACEUTICAL FORMULATIONS COMPRISING DEFERIPRONE

(71) Applicants: Chiesi Farmaceutici S.p.A., Parma (IT); Università degli Studi di Milano, Milan (IT)

(72) Inventors: Marisa Pertile, Parma (IT); Andrea Gazzaniga, Milan (IT); Matteo Cerea, Milan (IT); Micol Cirilli, Milan (IT)

(73) Assignees: Chiesi Farmaceutici S.p.A., Parma (IT); Università degli Studi di Milano, Milan (IT)

( * ) Notice: Subject to any disclaimer, the term of this patent is extended or adjusted under 35 U.S.C. 154(b) by 0 days.

(21) Appl. No.: 17/717,913

(22) Filed: Apr. 11, 2022

(65) Prior Publication Data

US 2023/0321060 A1    Oct. 12, 2023

(51) Int. Cl.
| | | |
|---|---|---|
| A61K 31/4412 | (2006.01) | |
| A61K 9/20 | (2006.01) | |
| A61K 47/14 | (2017.01) | |

(52) U.S. Cl.
CPC ........ *A61K 31/4412* (2013.01); *A61K 9/2031* (2013.01); *A61K 9/2036* (2013.01); *A61K 47/14* (2013.01)

(58) Field of Classification Search
CPC .............................. A61K 31/4412; A61K 47/14
See application file for complete search history.

(56) References Cited

U.S. PATENT DOCUMENTS

| | | | |
|---|---|---|---|
| 6,224,911 B1 * | 5/2001 | Chowhan | A61K 9/2846 |
| | | | 424/490 |
| 7,049,328 B2 | 5/2006 | Spino et al. | |
| 8,263,125 B2 | 9/2012 | Vaya et al. | |
| 8,268,352 B2 | 9/2012 | Vaya et al. | |
| 8,563,035 B2 | 10/2013 | Cifter et al. | |
| 8,703,156 B2 | 4/2014 | Spino et al. | |
| 10,780,055 B2 | 9/2020 | Sherman et al. | |
| 10,940,115 B2 | 3/2021 | Sherman et al. | |
| 10,940,116 B2 | 3/2021 | Sherman et al. | |
| 2006/0122273 A1 | 6/2006 | Spino et al. | |
| 2008/0085306 A1 | 4/2008 | Nangia et al. | |
| 2009/0023784 A1 | 1/2009 | Munnich et al. | |
| 2010/0255082 A1 | 10/2010 | Chauhan et al. | |
| 2011/0039911 A1 | 2/2011 | Pe'Ery | |
| 2012/0053212 A1 | 3/2012 | Shah | |
| 2012/0189692 A1 | 7/2012 | Cullen et al. | |
| 2013/0023569 A1 | 1/2013 | Spino et al. | |
| 2014/0314676 A1 | 10/2014 | Spino et al. | |
| 2014/0364491 A1 * | 12/2014 | Bortz | A61K 45/06 |
| | | | 514/494 |
| 2018/0036228 A1 | 2/2018 | Burke et al. | |
| 2019/0117581 A1 | 4/2019 | Sherman et al. | |
| 2019/0125682 A1 | 5/2019 | Sherman et al. | |
| 2020/0188309 A1 | 6/2020 | Sherman et al. | |
| 2020/0237674 A1 | 7/2020 | Sherman et al. | |
| 2020/0253945 A1 | 8/2020 | Sherman et al. | |
| 2020/0268672 A1 | 8/2020 | Sherman et al. | |
| 2021/0386677 A1 | 12/2021 | Sherman et al. | |

FOREIGN PATENT DOCUMENTS

| | | | | |
|---|---|---|---|---|
| CA | 2505476 | A1 | 5/2004 | |
| CA | 2819234 | A1 | 7/2012 | |
| CN | 101352438 | A | 1/2009 | |
| CN | 106983746 | A | 7/2017 | |
| IN | 247315 | | 4/1999 | |
| IR | 90-07-27-71996 | | 12/2011 | |
| WO | WO-9718805 | A1 | 5/1997 | |
| WO | WO-9825905 | A1 | 6/1998 | |
| WO | WO-0149266 | A2 | 7/2001 | |
| WO | WO-0202114 | A1 | 1/2002 | |
| WO | WO-2004006856 | A2 | 1/2004 | |
| WO | WO-2006017650 | A2 | 2/2006 | |
| WO | WO 2008/066862 | | 6/2008 | |
| WO | WO-2009104838 | A1 * | 8/2009 | ........... A61K 31/485 |
| WO | WO-2009155088 | A1 | 12/2009 | |
| WO | WO-2010005851 | A1 | 1/2010 | |
| WO | WO-2010069920 | A1 | 6/2010 | |
| WO | WO-2011032000 | A2 | 3/2011 | |
| WO | WO-2013075015 | A1 | 5/2013 | |
| WO | WO-2013139931 | A1 | 9/2013 | |
| WO | WO-2014072673 | A1 | 5/2014 | |
| WO | WO-2015087258 | A1 | 6/2015 | |
| WO | WO 2019/082128 | | 5/2019 | |

OTHER PUBLICATIONS

Agrawal, S., et al., "Mitochondrial iron dysregulation in mouse and human Huntington's disease brain, Presented at Society for Neuroscience," Nov. 11-15, 2017, Washington D.C., United States, 1 page.

Agrawal, M.B, et al., "Deferiprone (Kelfer), how to Make it Work More Widely, Effectively and Without Adverse Effects: An Indian Study." 1 page, 9*th* International Conference on Oral Chelation, Hamburg, Germany (1999).

Aguilar-De-Leyva, A., et al., "A New Deferiprone Controlled Release System Obtained by Ultrasound-assisted Compression," *Pharmaceutical Development and Technology* 19(6):728-734, Informa Healthcare, United Kingdom (Sep. 2014).

Al-Refaie, F.N., et al., "Oral Iron-chelating Therapy: the L1 Experience," *Baillière's Clinical Haematology* 7(4):941-963, Bailliere Tindall, United Kingdom (Dec. 1994).

(Continued)

*Primary Examiner* — Michael B. Pallay
(74) *Attorney, Agent, or Firm* — Sterne, Kessler, Goldstein & Fox P.L.L.C.

(57) ABSTRACT

The disclosure is directed to pharmaceutical compositions for oral administration comprising deferiprone. In particular, the disclosure is also directed to modified release tablets suitable either for twice daily administration or once daily administration. The disclosure is also directed to methods of making and using the same.

17 Claims, 4 Drawing Sheets

(56) References Cited

OTHER PUBLICATIONS

Anderson, L.J., et al., "Comparison of Effects of Oral Deferiprone and Subcutaneous Desferrioxamine on Myocardial Iron Concentrations and Ventricular Function in Beta-thalassaemia," *Lancet* 360: 516-520, Elsevier, United Kingdom (Aug. 2002).
Azarkeivan, A., et al., "Evaluation of gastric side effects of new form of Deferiprone, (L1; Enteric coated) in Thalassemia major patients," *Sci J Iran Blood Transfus Organ* 13(3): 163-169, Iranian Blood Transfusion Organization Research Center, Iran (2016).
Cabantchik, Z.I., et al., "Regional siderosis: a new challenge for iron chelation therapy," *Frontiers in Pharmacology* 4(167): 1-7, Frontiers, Switzerland (2013).
Chen, J., et al., "Iron Accumulates in Huntington's Disease Neurons: Protection by Deferoxamine," *PLOS one* 8(10):e77023, pp. 1-12, Public Library of Science, United States (2013).
Clinical Trials. Retrieved from the Internet: (URL: https://clinicaltrials.gov/ct2/results?term=deferiprone&no_unk=Y). (retrieved on Nov. 15, 2018.).
Cossu, G., et al., "Efficacy and safety of deferiprone for the treatment of pantothenate kinase-associated neurodegeneration (PKAN) and neurodegeneration with brain iron accumulation (NBIA): results from a four years follow-up," *Parkinsonism & Related Disorders* 20(6):651-654, Elsevier, Netherlands (2014).
Crosland, R.D., et al., "Action of Reactive Oxygen Species and Their Antagonists on Twitch Tension of the Rat Phrenic Nerve-diaphragm," *Pharmacology & Toxicology* 77(3):231-237, Nordic Pharmacological Society : Distributed by Blackwell Munksgaard, Denmark (Sep. 1995).
Eleftheriou A., "about thalassemia," thalassemia international federation, pp. 1-178 (2003).
Galanello, R., "Deferiprone in the treatment of transfusion-dependent thalassemia: a review and perspective," *Ther Clin Risk Manag.* 3(5):795-805, Dovepress, United Kingdom (2007).
Grady, R. W and Giardina, P.J., "Iron Chelation: Rationale for Combination Therapy," *Iron Chelators: New Development Strategies*, pp. 293-310 Ponte Vedra Beach, FL: Saratoga group (2000).
Grady, R.W., et al., "Iron Chelation: Combined Therapy May Be a Better Approach." 1 page, $9^{th}$ International Conference on Oral Chelation, Hamburg, Germany (1999).
Grubman, A., et al., "Mitochondrial Metals as a Potential Therapeutic Target in Neurodegeneration," *British Journal of Pharmacology* 171(8): 2159-2173, Wiley, United Kingdom (Apr. 2014).
Hatcher, H.C., et al., "Synthetic and Natural Iron Chelators: Therapeutic Potential and Clinical Use," *Future Medicinal Chemistry* 1(9), pp. 1-35 Future Science, United Kingdom (Dec. 2009).
Heli, H., et al., "Advances in Iron Chelation: an Update," *Expert Opinion on Therapeutic Patents* 21(6): 819-856, Informa Healthcare, United Kingdom (Jun. 2011).
Hoffbrand, A.V, "Oral Iron Chelation," *Seminars in Hematology* 33(1): 1-8, W.B. Saunders, United States (Jan. 1996).
Kakhlon, O., et al., "Iron Redistribution as a therapeutic strategy for treating diseases of localized iron accumulation," *Canadian Journal of Physiology and Pharmacology* 88(3):187-196, NRC Research Press, Canada (2010).
Kaul, D. and Taram, S.V., "Dual Control over release of a water soluble drug from compressed tablets," *Indian Journal of Pharmaceutical Sciences* 56(1);15-18, The Indian Pharmaceutical Society, India (1994).
Kaul, D. and Venkataram, S., "Sustained Release Tablet Formulation for a new Iron Chelator," *Drug Development and Industrial Pharmacy* 18(9):1023-1035, Taylor & Francis, United Kingdom (1992).
Kaul, D., et al., "Crystal Habit modifications and altered tableting characteristics," *International Journal of Pharmaceutics* 88(1-3):345-350, Elsevier, Netherlands (1992).
Kontoghiorghes, G.J., et al., "Safety Issues of Iron Chelation Therapy in Patients With Normal Range Iron Stores Including Thalassaemia, Neurodegenerative, Renal and Infectious Diseases," *Expert Opinion on Drug Safety* 9(2):201-216, Taylor & Francis, United Kingdom (Mar. 2010).
Kontoghiorghes, G.J., et al., "Benefits and Risks of Deferiprone in Iron Overload in Thalassaemia and Other Conditions: Comparison of Epidemiological and Therapeutic Aspects With Deferoxamine," *Drug Safety* 26(8):553-584, Springer International, New Zealand (2003).
Kontoghiorghes, G.J., et al., "Risk/benefit Assessment, Advantages Over Other Drugs and Targeting Methods in the Use of Deferiprone as a Pharmaceutical Antioxidant in Iron Loading and Non Iron Loading Conditions," *Hemoglobin* 33(5):386-397, Informa Healthcare, United Kingdom (2009).
Kontoghiorghes, G.J., et al., "The Role of Iron and Chelators on Infections in Iron Overload and Non Iron Loaded Conditions: Prospects for the Design of New Antimicrobial Therapies," *Hemoglobin* 34(3):227-239, Informa Healthcare, United Kingdom (Jun. 2010).
Kwiatkowski, A., et al., "Long-term Improvement Under Deferiprone in a Case of Neurodegeneration With Brain Iron Accumulation," *Parkinsonism and Related Disorders* 18(1):110-112, Elsevier Science, United Kingdom (Jan. 2012).
NCT02465489, Trial No. LA51-0115, "Single-dose pharmacokinetic study of deferiprone extended release tablets versus Ferriprox immediate release tablets under fasting and fed condition in healthy volunteers," ClinicalTrials.gov, Phase 1, accessed at URL:[https://clinicaltrials.gov/ct2/show/NCT02465489?term=LA51-0115&draw=1&rank=1] on Jul. 20, 2020, 18 pages.
Levy, M., et al., "Pilot safety trial of deferiprone in 10 subjects with superficial siderosis," *Stroke* 43(1): 120-124, Lippincott Williams & Wilkins, United States (2012).
Moreau, C., et al., "Could conservative iron chelation lead to neuroprotection amyotrophic lateral sclerosis?," *Antioxid Redox* 29(8), 17 pages Mary Ann Liebert, United States (2018).
Morel, I., et al., "Antioxidant and Free Radical Scavenging Activities of the Iron Chelators Pyoverdin and Hydroxypyrid-4-ones in Iron-loaded Hepatocyte Cultures: Comparison of Their Mechanism of Protection With That of Desferrioxamine," *Free Radical Biology and Medicine* 13(5):499-508, Elsevier Science, United States (Nov. 1992).
NCT02442310, Comparison of Deferiprone Delayed Release tablets and Deferiprone Oral Solution in Healthy Volunteers, ClinicalTrials.gov, published May 13, 2016, accessed at https://clinicaltrials.gov/ct2/show/NCT02442310, accessed on May 25, 2017, 4 pages.
Peng, C-T., et al., "Safety Monitoring of Cardiac and Hepatic Systems in Beta-thalassemia Patients With Chelating Treatment in Taiwan," *European Journal of Haematology* 70(6):392-397, Blackwell, United Kingdom (Jun. 2003).
Pennell, D.J., et al., "Randomized Controlled Trial of Deferiprone or Deferoxamine in Beta-thalassemia Major Patients With Asymptomatic Myocardial Siderosis," *Blood* 107(9):3738-3744, American Society of Hematology, United States (May 2006).
Reeder, B.J., et al., "Tyrosine as a Redox-active Center in Electron Transfer to Ferryl Heme in Globins," *Free Radical Biology and Medicine* 44(3):274-283, Elsevier Science, United States (Feb. 2008).
Sheth, S., "Iron Chelation: an update." *Curr Opin Hematol* 21(0), pp. 1-7 Wolters Kluwer, Netherlands (2014).
Song, D., et al., "Systemic administration of the iron chelator deferiprone protects against light-induced photoreceptor degeneration in the mouse retina," *Free Radical Biology and Medicine* 53(1):64-71, Elsevier, Netherlands (2012).
Spiegel, B.M., et al., "Understanding gastrointestinal distress: a framework for clinical practice," *Am J Gastroenterol* 106(3):380-385, Nature Publishing Group, United States (2011).
Stumpf, J.L, "Deferasirox," *American Journal of Health-System Pharmacy* 64(6):606-616, American Society of Health-System Pharmacists, United States (Mar. 2007).
Thalassemia therapy, Deferasirox and Deferiprone are useful for iron overload in thalassemia major, Medical letter on the CDC & FDA; 88, 3 pages (2006).
Thompson, M.G., et al., "Antibacterial Activities of Iron Chelators Against Common Nosocomial Pathogens," *Antimicrobial Agents*

(56) References Cited

OTHER PUBLICATIONS and Chemotherapy 56(10):5419-5421, American Society for Microbiology, United States (Oct. 2012).

Transfusion medicine, Deferiprone shows potential for first-line iron chelation drug obesity, fitness & wellness week; 1498, 3 pages (2005).

Tsou, A.Y., et al., "Pharmacotherapy for Friedreich Ataxia," *CNS Drugs* 23(3):213-223, Springer International, New Zealand (2009).

Venkataram, S and Khohlokwane, M, "Microencapsulation of an Iron Chelator for Sustained Release and Crystal Habit Modification," *Journal of Microencapsulation* 13(5):519-525, Informa Healthcare, United Kingdom (Sep.-Oct. 1996).

Waldmeier, P.C., et al., "Inhibition of Catechol-o-methyltransferase (Comt) as Well as Tyrosine and Tryptophan Hydroxylase by the Orally Active Iron Chelator, 1,2-dimethyl-3-hydroxypyridin-4-one (L1, Cp20), in Rat Brain in Vivo," *Biochemical Pharmacology* 45(12):2417-2424, Elsevier Science, United Kingdom (Jun. 1993).

Ware, H.M. and Kwiatkowski, J.L., "Evaluation and Treatment of Transfusional Iron Overload in Children," *Pediatr Clin N Am* 60:1393-1406, Elsevier, Netherlands (2013).

Weigel, K.J., et al., "Iron chelation and multiple sclerosis," *ASN Neuro* 6(1): 44-63, Sage Publications, United States (2014).

Whiteside, D.P., et al., "Pharmacokinetic Disposition of the Oral Iron Chelator Deferiprone in the Domestic Pigeon (*Columba livia*)," *Journal of Avian Medicine and Surgery* 21(2):121-129, Association of Avian Veterinarians, United States (Jun. 2007).

NCT02728843, "Study of Parkinson's Early Stage with Deferiprone (SKY)", ClinicalTrials.gov, accessed at https://clinicaltrials.gov/ct2/show/NCT02728843?term=02728843&rank=1, accessed on Jan. 4, 2019, 7 pages.

Hoffbrand, A. V., et al., "Role of Deferiprone in chelation therapy for transfusional iron overload," *Blood* 102(1):17-24, American Society of Hematology, United States (2003).

Morales, N.P., et al., "Bioequivalence study of a film-coated tablet of deferiprone in healthy Thai volunteers," *International Journal of Clinical Pharmacology and Therapeutics* 47(5):358-364, American Society of Pharmacology & Therapeutics, United States (2009).

Rujivipat, S., and Bodmeier, R., "Improved Drug delivery to the lower intestinal tract with tablets compression-coated with enteric/nonenteric polymer powder blends," *European Journal of Pharmaceutics and Biopharmaceutics* 76:486-492, Elsevier, Netherlands (2010).

"Clinical Trial: Comparison of Deferiprone Delayed Release Tablets and Deferiprone Oral Solution in Healthy Volunteers." Indian eGov Newswire, May 26, 2015.Infotrac Newsstand, http://link.galegroup.corn/apps/doc/A414977911/STND?u-tplmain&SID=STND&xid=e7ec89ba.

Clinical Trials, "Comparison of Deferiprone Delayed Release Tablets and Deferiprone Oral Solution in Healthy Volunteers," available at, https://clinicaltrials.gov/ct2/history/NCT02442310?V_4=View#StudyPageTop, (last accessed on Jan. 30, 2020), Published May 13, 2016, pp. 1-25.

Felton, L. (Ed.), "Remington: Essentials of Pharmaceutics," Chapters 2, 30-32 and Appendix B., Pharmaceutical Press, London, UK, (2013).

Hilton, A., et al., "Use of Hydoxypropyl Methylcellulose Acetate Succinate in an Enteric Polymer Matrix To Design Controlled-Release Tablets of Amoxicillin Trihydrate," *Journal of Pharmaceutical Sciences*, 82(7): 737-743, American Pharmaceutical Association, United States (1993).

Ferriprox® (deferiprone) tablets, for oral use, prescribing information, Oct. 2011, accessed at URL:[https://www.accessdata.fda.gov/drugsatfda_docs/label/2011/021825lbl.pdf] on Jul. 19, 2019, 7 pages.

Co-pending U.S. Appl. No. 17/717,922, inventors Pertile, Marisa, et al., filed on Apr. 11, 2022.

Cohen, E.R., et al., "Safety profile of the oral iron chelator deferiprone: a multicenter study," *Br J Haematology* 108:305-312, Blackwell Science Ltd., United States (2000).

European Pharmacopoeia 4$^{th}$ Ed., Supplement 4.3, p. 2891, Directorate for the quality of Medicines of the Council of Europe, France (2003).

Galanello, R., et al. "A prospective randomized controlled trial on the safety and efficacy of alternating deferoxamine and deferiprone in the treatment of iron overload in patients with thalassemia," *Haematologica* 91(9):1241-1243, Ferrata Storti Foundation, Italy (2006).

Hider, R.C. and Hoffbrand, A.V., "The Role of Deferiprone in Irone Chelation," *N Engl J Med.* 379:2140-2150, Massachusetts Medical Society, United States (2018).

Maggio, A., et al., "Deferiprone versus deferoxamine in patients with thalassemia major: a randomized clinical trial," Blood Cells Mol Dis. 28(2):196-208, Elsevier, Netherlands (2002).

Aburahma, M. H., and Badr-Eldin, S. M., "Compritol 888 ATO: a multifunctional lipid excipient in drug delivery systems and nanopharmaceuticals," Expert Opin Drug Deliv 11(12):1865-1883, Taylor & Francis, United Kingdom (2014).

Campos-Aldrete, M. A., et al., "Influence of the viscosity grade and the particle size of HPMC on metronidazole release from matrix tablets," European Journal of Pharmaceutics and Biopharmaceutics 43(2):173-178, Elsevier, Netherlands (1997).

Cao, Q.-R., et al., "A formulation approach for development of HPMC-based sustained release tablets for tolterodine tartrate with a low release variation," Drug Development and Industrial Pharmacy 39(11):1720-1730, Informa Healthcare, United States (2013).

El-Halim, S. M. A., et al., "Comparative study on the different techniques for the preparation of sustained-release hydrophobic matrices of a highly water-soluble drug," Drug Discov Ther 4(6):484-492, International Advancement Center for Medicine & Health Research Co., Ltd., Japan (2010).

Li, F.-Q., et al., "In vitro controlled release of sodium ferulate from Compritol 888 ATO-based matrix tablets," Int J Pharm 324(2):152-157, Elsevier, Netherlands (2006).

Roberts, M., et al., "Development and evaluation of sustained-release Compritol® 888 ATO matrix mini-tablets," Drug Dev Ind Pharm 38(9):1068-1076, Informa Pharmaceutical Science, United Kingdom (2012).

Roberts, M., et al., "Preparation and characterization of Compritol 888 ATO matrix tablets for the sustained release of diclofenac sodium," Pharmaceutical Development and Technology 20(4):507-512, Taylor & Francis, United Kingdom (published online Dec. 2013; published in print Jun. 2015).

Rosiaux, Y., et al., "Optimizing a wet granulation process to obtain high-dose sustained-release tablets with Compritol 888 ATO," Drug Dev Ind Pharm 41(10):1738-1744, Informa Pharmaceutical Science, United Kingdom (2015).

Vazquez, M.-J., et al., "Atenolol release from hydrophilic matrix tablets with hydroxypropylmethylcellulose (HPMC) mixtures as gelling agent: effects of the viscosity of the HPMC mixture," European Journal of Pharmaceutical Science 4(1):39-48, Elsevier, Netherlands (1996).

Beeckmans, D., et al., "Altered duodenal bile salt concentration and receptor expression in functional dyspepsia," United European Gastroenterol J 6(9):1347-1355, John Wiley & Sons, United States (Nov. 2018).

Dahlgren, D., et al., "Fasted and fed state human duodenal fluids: Characterization, drug solubility, and comparison to simulated fluids and with human bioavailability," Eur J Pharm Biopharm 163:240-251, Elsevier, Netherlands (Jun. 2021).

\* cited by examiner

MODIFIED RELEASE PHARMACEUTICAL FORMULATIONS COMPRISING DEFERIPRONE

FIELD OF THE DISCLOSURE

The disclosure relates to pharmaceutical formulations comprising the iron chelator deferiprone. In particular, the disclosure is directed to modified release formulations suitable for twice-a-day or once-a-day oral administration for the treatment of patients suffering from for example, thalassemia, sickle cell anemia, hemochromatosis, and myelodysplasia.

BACKGROUND OF THE DISCLOSURE

Deferiprone, also known as 3-hydroxy-1,2-dimethylpyridin-4-one, is a bidentate ligand which binds to iron in a 3:1 molar ratio.

It is used in the treatment of generalized iron overload, particularly in conditions where frequent blood transfusions lead to iron overload including, e.g., thalassemia and Sickle Cell Disease.

The introduction of deferiprone in the current therapy has represented an important advancement as it Liver Iron Concentration (LIC) and cardiac iron overload. In particular, Maggio A., et al., Blood Cells Mol Dis. 2002, 28(2):196-208 and Galanello R., et al., Haematologica. 2006, 91(9):1241-1243 suggested that deferiprone monotherapy seems to be superior to deferoxamine monotherapy in improving myocardial siderosis and cardiac function.

With regards to safety, the most frequent adverse events are gastrointestinal disorders due to gastrointestinal irritation. Such discomfort could cause patients to refrain from taking the medication, leading to a worsening of their condition. Other observed adverse events are musculoskeletal disorders (arthralgia), Alanine Aminotransferase (ALT) increase, agranulocytosis and neutropenia.

Agranulocytosis seems to be an idiosyncratic response and it is more frequent in the first year of treatment. The incidence of neutropenia and agranulocytosis is stable and seems to be not related with dose (Hider R C et al N Engl J Med. 2018; 379:2140-2150).

Deferiprone is endowed with a long half-life of 2-3 hour) and an unpleasant bitter taste too.

Said drug is sold as Immediate Release (IR) 500 mg and 1000 mg tablets, as well as a 100 mg/ml liquid formulation, generally, under the trade name Ferriprox®.

In view of its pharmacological and ADME profile, and in order to improve the compliances of the patients, recently, deferiprone has also been launched commercially as 1000 mg Delayed Release (DR) tablets for oral administration.

Said tablets are suitable for a twice daily administration being bioequivalent in the steady state to the same daily dose of an immediate release tablet administered three times daily.

Said tablets are also debossed with a score line, to make it easy for the patient to break the tablets into two approximately equal parts for dosing flexibility.

The composition of the DR tablets has been disclosed in WO 2019/082128, and it comprises: (a) a core comprising the active pharmaceutical ingredient and a releasing controlling enteric polymer, and (b) an enteric coating.

Upon oral administration, the enteric coating makes the dissolution in the stomach negligible and hence subsequent dissolution of the physiologically active substance at weakly acidic to weakly alkaline pH (e.g., pH 4.5 to 8), which corresponds to dissolution in the small intestine and, especially in the duodenum to ileum, is facilitated.

To sustain the release, in the case of the marketed deferiprone product, an enteric polymer in the tablet core, hydroxypropyl methylcellulose acetate succinate (HPMC-AS), is used.

However, HPMC-AS has a pH-dependent solubility.

This could lead to a release influenced by the external environment that the formulation has to face during transit along the regions in which the release of the active agent takes place, which are characterized by physiological fluids having different pH's. Hence, the release can be less predictable in view of random microenvironmental variation of the pH.

Therefore, it would be advantageous to provide a tablet suitable for twice a day oral administration, with improved properties in terms of reproducibility of the expected release profiles.

It would even be more advantageous, for the compliance of the patient, to provide tablets having the above properties but with an even more prolonged release, possibly suitable for once-day oral administration.

The technical solution is provided by the present disclosure.

SUMMARY

In one aspect is provided a pharmaceutical formulation comprising deferiprone and a modifying release agent comprising glyceryl esters of long fatty acids, wherein the tablet is suitable for twice-a-day or once-a-day oral administration. In some aspects, the modifying release agent is selected from the group consisting of glyceryl palmitostearate, glyceryl monostearate, glyceryl dibehenate, and combinations thereof. In some aspects, the modifying release agent is glyceryl dibehenate.

In some aspects, the modifying release agent is a mixture of glyceryl esters of behenic acid. A commercial example of a mixture of glyceryl esters of behenic acid is Compritol®.

Is some aspects, the pharmaceutical formulations could be, for instance, in form of gastroresistant capsules, enteric coated capsules, or tablets. In some aspects, the pharmaceutical formulation can be in the form of enteric coated tablets.

In another aspect is provided a modified release tablet comprising: (a) a core comprising deferiprone in an amount of about 85.0% to about 95.0%% by weight of the tablet, a modifying release agent comprising glyceryl esters of long fatty acids in an amount of about 1.0% to about 2.0% by weight of the tablet, a lubricant and/or glidant in an amount of about 0 to about 2.0% by weight of the tablet, and additional pharmaceutically acceptable excipients in an amount of about 0 to 13.0% by weight of the tablet; and (b) an enteric coating; wherein the tablet is suitable for twice a day oral administration In another aspect is provided a modified release enteric coated pharmaceutical formulation for twice-a-day oral administration, wherein the pharmaceutical formulation is a tablet, and wherein the core of the tablet comprises deferiprone in an amount of about 85 to 95%, glyceryl esters of long fatty acids as a modified release agent in an amount of about 1.0 and 2.0%, a lubricant and/or glidant in an amount of about 1.0 to 2.0%, and other suitable pharmaceutically acceptable excipients in an amount of about 1.0 to 13%, wherein all the amounts calculated by weight on the total weight of the formulation.

In another aspect is provided a modified release tablet comprising: (a) a core comprising deferiprone in an amount of about 85.0% to about 88.0% by weight of the tablet, a modifying release agent comprising glyceryl esters of long fatty acids in an amount of about 8.0% and about 15.0% by weight of the tablet, a lubricant and/or glidant in an amount from about 0 to about 2.0% by weight of the tablet, and additional pharmaceutically acceptable excipients in an amount of about 0 to about 5.0% by weight of the tablet; and (b) an enteric coating; wherein the tablet is suitable for once a day oral administration.

In another aspect is provided a modified release enteric coated pharmaceutical formulation for once-a-day oral administration, wherein the core of the tablet comprises deferiprone in an amount of about 85 to 88%, glyceryl esters of long fatty acids as a modified release agent in an amount of about 8.0 and 15.0%, a lubricant and/or glidant in an amount of about 0 to 2%, and optionally other suitable pharmaceutically acceptable excipients in an amount of about 0 to 5%, wherein all the amounts calculated by weight on the total weight of the formulation.

In some aspects, the modifying release agent is selected from the group consisting of glyceryl palmitostearate, glyceryl monostearate, glyceryl dibehenate, and combinations thereof. In some aspects, the modifying release agent is glyceryl dibehenate.

In some aspects, the lubricant is selected is selected from the group consisting of magnesium stearate, calcium stearate, stearic acid, sodium stearyl fumarate, talc, and a combination thereof. In some aspects, the lubricant is magnesium stearate.

In some aspects, the glidant is selected from the group consisting of colloidal silicon dioxide, starch and talc and combination thereof. In some aspects, the glidant is colloidal silicon dioxide.

In some aspects, the additional pharmaceutically acceptable excipients are selected from pH adjusting agents and bulking agents.

In some aspects, the enteric coating comprises an enteric polymer, a diluent, and optionally a plasticizer. In some aspects, the enteric coating comprises an ethacrylic acid-ethyl acrylate copolymer (1:1) dispersion in water and propylene glycol. In some aspects, the enteric coating comprises methacrylic acid-methacrylate copolymer (1:1) in an alcoholic solution with triethyl citrate.

In some aspects, the core of the tablet comprises from 500 to 1500 mg of deferiprone.

In some aspects, the core of the tablet comprises 1000 mg of deferiprone.

In some aspects, other suitable pharmaceutically acceptable excipients may belong to the classes of pH adjusting agents, and bulking agents.

In another aspect is provided a process for the preparation of the modified release tablet described herein, comprising:
(i) mixing deferiprone with the modifying release agent and the additional pharmaceutically acceptable excipients, if present, to form a mixture;
(ii) wet-granulating the mixture obtained in step (i) in a high shear granulator followed by drying and screening to produce a granulate;
(iii) mixing the granulates obtained in step (ii) with the lubricant/glidant to form a mixture;
(iv) compressing the mixture obtained in step (iii) to form a tablet; and
(v) coating the tablet.

In another aspect is provided a process for the preparation of the modified release tablet described herein, comprising:
(i) mixing deferiprone with the modified release agent and the additional pharmaceutically acceptable excipients, if present;
(ii) adding the lubricant/glidant by further mixing to form a mixture;
(iii) directly compressing the mixture obtained in step (ii) to form a tablet; and
(iv) coating the tablet.

In another aspect is provided the modified release tablet as described herein for use in the treatment of diseases which cause an overload of iron, or for the prevention and/or treatment of diseases which are caused by an overload of iron. In some aspects, the disease is thalassemia or sickle cell anemia. In some aspects, the iron overload is transfusional iron overload.

In another aspect is provided a method of treating a disease which causes an overload of iron, comprising administering the modified release tablet as described herein. In some aspects, the disease is thalassemia or sickle cell anemia. In some aspects, the iron overload is transfusional iron overload.

In another aspect is provided a method of treating and/or preventing a disease which is caused by an overload of iron, comprising administering the modified release tablet as described herein. In some aspects, the iron overload is transfusional iron overload.

In another aspect is provided the modified release tablet as described herein for the manufacture of a medicament for the treatment of diseases which cause an overload of iron, or for the prevention and/or treatment of diseases which are caused by an overload of iron. In some aspects, the disease is thalassemia or sickle cell anemia. In some aspects, the iron overload is transfusional iron overload.

In another aspect is provided a method for the treatment of diseases which cause an overload of iron, or for the prevention and/or treatment of diseases which are caused by an overload of iron in a patient in a need thereof, said method comprising orally administering the claimed pharmaceutical composition.

In another aspect is provided a method for reducing gastric distress or the risk of gastric distress in a patient in need of deferiprone treatment, comprising orally administering to the patient a modified release tablet comprising: (a) a core comprising deferiprone in an amount of about 85.0% to about 88.0% by weight of the tablet, a modifying release agent comprising glyceryl esters of long fatty acids in an amount of about 8.0% and about 15.0% by weight of the tablet, a lubricant and/or glidant in an amount from about 0 to about 2.0% by weight of the tablet, and additional pharmaceutically acceptable excipients in an amount of about 0 to about 5.0% by weight of the tablet; and (b) an enteric coating; wherein the tablet is suitable for once a day oral administration.

In another aspect is provided a method for reducing gastric distress or the risk of gastric distress in a patient in need of deferiprone treatment, comprising orally administering to the patient a modified release enteric coated pharmaceutical formulation, wherein the pharmaceutical formulation is a tablet, and wherein the core of the tablet comprises deferiprone in an amount of about 85 to 88%, glyceryl esters of long fatty acids as a modified release agent in an amount of about 8.0 and 15.0%, a lubricant and/or glidant in an amount of about 0 to 2%, optionally other suitable pharmaceutically acceptable excipients in an amount of about 0 to 5%, wherein all the amounts calculated by weight on the total weight of the formulation, and wherein the tablet is suitable for once-a-day oral administration.

DEFINITIONS

Figure 1:
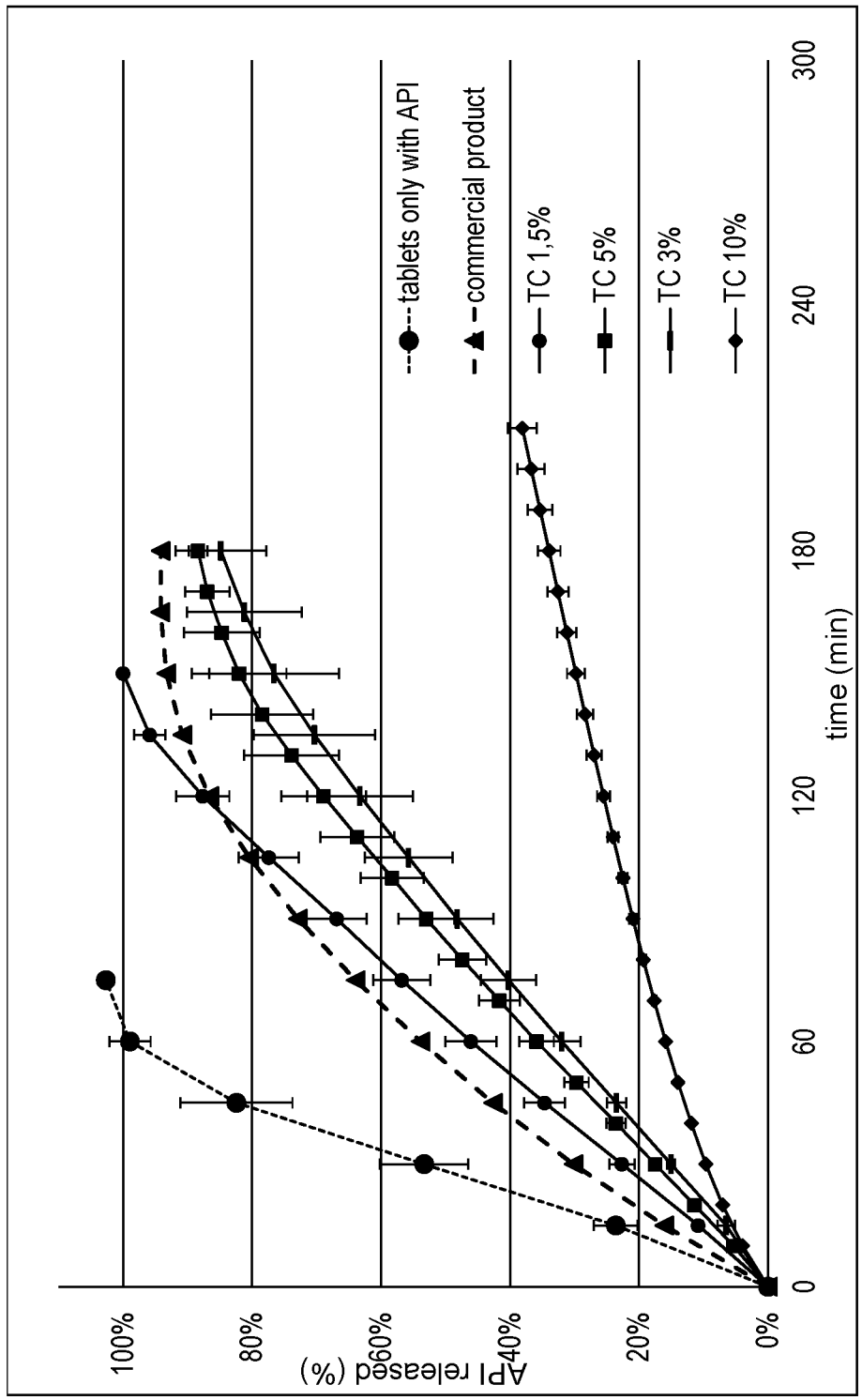
FIG. 1: Dissolution tests of glyceryl esters of behenic acid (e.g., Compritol®) formulations carried out in 900 ml of pH 6.8 medium, basket (apparatus 1) having rotational speed of 100 rpm. The line with a triangular indicator is referred to the commercial product.

As used herein, the indefinite articles "a" or "an" should be understood to refer to "one or more" of any recited or enumerated component. For example, "a tablet" refers to one or more tablets.

Also as used herein, "and/or" refers to and encompasses any and all possible combinations of one or more of the associated listed items, as well as the lack of combinations when interpreted in the alternative ("or").

When the term "about" is used in conjunction with a numerical value or range, it modifies that value or range by extending the boundaries above and below the numerical values set forth. The term "about" is used herein to modify a numerical value above and below the stated value by a variance of 10 percent, up or down (higher or lower), i.e., ±10%, unless a different variance is indicated (e.g., ±30%, ±20%, ±5%, ±1%, etc.).

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed is also disclosed. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

The terms "iron overload" or "overload of iron" are used interchangeably herein and refer to medical conditions where the body contains or stores too much (or "excess") iron. An example is transfusional iron overload, where the excess iron is introduced by one or more blood transfusions.

Wherever aspects are described herein with the language "comprising," otherwise analogous aspects described in terms of "consisting of and/or "consisting essentially of are also provided. To the extent that the term "includes" or "including" is used in the specification or the claims, it is intended to be inclusive in a manner similar to the term "comprising" as that term is interpreted when employed as a transitional word in a claim.

As used herein, the term "active ingredient" or "active pharmaceutical ingredient" (API) or "drug" are used as synonymous and mean any component that is intended to furnish pharmacological activity or other direct effect in the diagnosis, cure, mitigation, treatment, or prevention of disease, or to affect the structure or any function of the body of man or other animals.

With the term "glyceryl esters of long fatty acids" is meant a substance wherein one two, or three alcoholic groups of the glycerol moiety are esterified with long chain saturated fatty acids $C_{14}$-$C_{22}$, and mono-, di-, triglycerides are formed or mixture thereof.

In the present context, the term "hydrophilic" describes that something 'likes water', i.e. a hydrophilic molecule or portion of a molecule is one that typically is electrically polarized and capable of forming hydrogen bonds with water molecules, enabling it dissolve more readily in water than in oil or other "non-polar" solvents.

Conversely, the term "hydrophobic" denotes a compound tending to be electrically neutral and non-polar, and thus preferring other neutral and nonpolar solvents or molecular environments.

In the present context, the term "amphiphilic" describes a molecule having a polar water-soluble group attached to a water-insoluble hydrocarbon chain. Thus, one end of the molecule is hydrophilic (polar) and the other is hydrophobic (non-polar).

For "pH dependent solubility" it is meant a substance having different solubilities at different pHs. These pH-dependent solubility differences lead to pH-dependent dissolution profiles.

The expression "insoluble or poorly water soluble" refers to a substance having a solubility in water as defined in the European Pharmacopoeia Ed. 4$^{th}$, 2003, page 2891.

"Core" or "tablet core" as used herein comprises an active ingredient, e.g., deferiprone, and one or more excipients compressed into an uncoated tablet. The core can be coated with various coatings, including an enteric coating.

In the present context, the terms "controlled release", "prolonged release", "modified release" and "delayed release" are intended to be equivalent terms covering any type of release of deferiprone from a composition of the disclosure that is appropriate to obtain a specific therapeutic or prophylactic response after administration to a subject". The terms refer to protecting an active ingredient, e.g., deferiprone, from rapid release at acidic pH, e.g., in the stomach, while enabling the active ingredient to be released at a higher rate at a higher pH, e.g., in the intestines. In some aspects, DR will be understood to mean that, when tested in USP apparatus 2 at 75 rpm, the extent of dissolution will be around 20±5 at 1 hour in 0.1N HCl, and the rate of dissolution will be substantially higher (e.g., over 30%, e.g. over 40%, in 1 hour) in phosphate buffer with pH 6.8 than the rate of dissolution in 0. 1N HCl.

"Disintegrant" as used herein refers to an excipient that is insoluble in water, but swells when wetted to cause a tablet to disintegrate.

"Dissolution" as used herein refers to the process by which a solute forms a solution in a solvent.

"Enteric coat" or "enteric coating" as used herein refers to a coating comprising an enteric polymer. An enteric coating can serve to prevent or delay a tablet's dissolution or disintegration in a gastric environment.

"Enteric coated tablet" means a tablet having a core comprising an active ingredient, which is coated with an enteric coating.

"Enteric polymer" as used herein is understood to mean a polymer that is relatively insoluble at the acidic pH of the fasted stomach (e.g., about pH 1 to about pH 4), but soluble at higher pH (e.g., about pH 4.5 to about pH 8), which corresponds to the pH in the small intestine or thereafter, particularly in the duodenum or ileum.

The terms "fillers", "diluents" and "bulking agents" are used as synonymous.

With the term "bioequivalence" it is meant the absence of a significant difference between the bioavailability, i.e., the extent of absorption and peak concentration, between two pharmaceutical drug products (e.g., a test product and a reference product) over the course of a period of time, at the same dose and under the same conditions, The determination of whether or not a test product is bioequivalent to a reference product is determined by performing a study, referred to as a bioequivalence or comparative bioavailability study, in a group of subjects, usually about 18-36 subjects or more, under controlled conditions.

The study can be done in a "crossover" design, which means that the study is done in 2 or more phases, usually at least a week apart, depending in part on the half-life of the drug. In the first phase, half the subjects are randomly assigned to ingest the test product first and the other half ingest the reference product first. In the second phase, each subject ingests the alternate product.

In each phase, blood samples are drawn from each subject, on a predetermined schedule after ingestion of the test product. The blood samples are then analyzed to determine serum concentrations of the drug (test product, e.g., deferiprone) at each time point. For example, drugs are bioequivalent if they enter circulation at the same rate when given in similar doses under similar conditions. Parameters often used in bioequivalence studies are $t_{max}$, $C_{max}$, $C_{min}$, $AUC_{0-infinity}$, $AUC_{0-t}$.

In the present context "$t_{max}$" denotes the time to reach the maximal plasma concentration ($C_{max}$) after administration; $AUC_{0-infinity}$ denotes the area under the plasma concentration versus time curve from time 0 to infinity; $AUC_{0-t}$ denotes the area under the plasma concentration versus time curve from time 0 to time t; W50 denotes the time where the plasma concentration is 50% or more of $C_{max}$; W75 denotes the time where the plasma concentration is 75% or more of $C_{max}$; and MRT denotes mean residence time for tacrolimus.

"Fasted state" as used herein refers to abstinence from food for a defined period of time after a meal (typically, at least several hours, e.g., 4 or 6 hours, after a meal).

"Fed state" as used herein refers to administration with a meal or soon after a meal (e.g., within about 1 hour).

The term "chemical stable" refers to stability of the active agent in the formulation, wherein changes in the drug assay values and/or impurities content are equal to or lesser than 5%, preferably lesser than 3%, during storage at 25° C. and 60% relative humidity (RH), or 40° C. and 75% RH, for at least 1 month.

The term "vitro-in vivo correlation (IVIVC)" refers an in vitro dissolution test that is predictive of the in vivo performance of the drug product.

"Gastric distress" as used herein refers to discomfort of the gastrointestinal (GI) tract, e.g., one or more of pain, cramping, bloating, nausea, indigestion, heartburn, and gas.

"Half tablet" as used herein means either of the two parts of a tablet obtained by splitting the tablet into two parts of equal or approximately equal weight. In some aspects, a half tablet is from about 40% to about 60% by weight of the whole tablet from which the half was derived. In some aspects, the approximately equal weight of each half tablet is about 45-55% of the total weight of the whole tablet.

"Percent" or "%" as used herein refers to weight percentage (w/w) unless otherwise specified.

"Scored tablet" as used herein refers to a tablet that is debossed with one or more lines, also known as a "score line", to facilitate splitting the tablet, e.g., to enable administration of a half tablet. In some aspects, the tablet can be scored with two, three, four, or more score lines.

"Tablet" as used herein refers a solid oral pharmaceutical dosage form. In some aspects, the tablet is a compressed tablet.

"Whole tablet" means a complete tablet, i.e., not broken or split into parts.

Terms such as "treating" or "treatment" or "to treat" or "ameliorating" or "alleviating" or "to alleviate" can refer to both 1) therapeutic measures that cure, slow down, lessen symptoms of, reverse, and/or halt progression of a diagnosed pathologic condition or disorder and 2) prophylactic or preventative measures that prevent, reduce the incidence of, reduce the risk of, and/or slow the development of a targeted pathologic condition or disorder. Thus, those in need of treatment include those who already have the disorder; those prone to developing the disorder; and those in whom the disorder is to be prevented. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those who already have the condition or disorder as well as those prone to developing the condition or disorder or those in which the condition or disorder is to be prevented or incidence reduced.

By "subject" or "individual" or "patient," is meant any human subject, for whom diagnosis, prognosis, treatment, or therapy is desired.

By "therapeutically effective dose or amount" or "effective amount" is intended an amount of active pharmaceutical ingredient, e.g., deferiprone, that when administered brings about a positive therapeutic response with respect to treatment of or reducing the risk of a disease in a subject to be treated.

It will be understood that the deferiprone DR tablets used as the "reference" or "reference product" herein are Ferriprox® tablets (1000 mg) as approved by FDA and sold in the United States.

DETAILED DESCRIPTION

The present disclosure provides pharmaceutical formulations for the prevention and/or treatment of diseases which are caused by an overload of iron, especially compositions providing modified release of the active ingredient. In some aspects, the pharmaceutical formulations are tablets. In some aspects, the pharmaceutical formulations are modified release tablets.

The active ingredient in the disclosed pharmaceutical formulations is deferiprone.

However, within the scope of the present disclosure is deferiprone in any physical form (crystals, amorphous powder, any possible polymorphs, any possible solvate. Included are also pharmaceutically acceptable salts and/or solvates thereof. In some aspects, deferiprone is used as a base in its anhydrous form.

Compositions

In one aspect is provided a pharmaceutical formulation comprising deferiprone and a modifying release agent comprising glyceryl esters of long fatty acids, wherein the tablet is suitable for twice-a-day or once-a-day oral administration. In some aspects, the modifying release agent is selected from the group consisting of glyceryl palmitostearate, glyceryl monostearate, glyceryl dibehenate, and combinations thereof. In some aspects, the modifying release agent is glyceryl dibehenate.

In some aspects is provided a use of glyceryl esters of long fatty acids, as modified release agent to provide a pharmaceutical formulation comprising deferiprone as active ingredient, suitable for twice-a-day or once-a-day oral administration.

In some aspects, the pharmaceutical formulations are preferably in form of tablets.

In fact, by using Compritol® 888 ATO as exemplary excipient, It has been found that a relatively small variation of the amount of the modifying release agent (e.g., glyceryl esters of behenic acid, commercially available as Compritol® 888 ATO) may transform a formulation comprising deferiprone that is suitable for twice-a-day oral administration into a formulation comprising deferiprone that is suitable for once-a-day administration.

In some aspects, the glyceryl esters of long fatty acids are selected from the group consisting of glyceryl palmitostearate, glyceryl monostearate, glyceryl dibehenate, and mixtures thereof.

Glyceryl dibehenate is a water-insoluble mixture of glyceryl esters of behenic acid commercially available as Compritol® 888 ATO from Gattefossé SAS, Saint-Priest Cedex, France.

Glyceryl palmitostearate is commercially available as Precirol® 5 ATO from Gattefossé SAS, Saint-Priest Cedex, France as well.

Glyceryl monostearate is a monoglyceride commercially available from Sigma Aldrich GmbH (Germany).

In some aspects, the modifying release agent is glyceryl dibehenate (e.g., Compritol® 888 ATO).

Deferiprone can cause gastric irritation if released in the fasted stomach, and some degradation by acidic hydrolysis is possible.

Therefore, in some aspects, pharmaceutical formulations could be, for instance, in form of gastroresistant capsules or enteric coated tablets. In some aspects, the pharmaceutical formulations can be in the form of enteric coated tablets.

In some aspects, the disclosed modified release tablet contains an enteric coating. In some aspects, the enteric coating serves both to delay dissolution of deferiprone and to avoid dissolution in the stomach, in particular the stomach of a fasted patient.

Due to the enteric coating, the disclosed modified release tablets have a negligible dissolution in the fasted stomach but will more rapidly dissolve in the intestines.

In another aspect is provided a modified release tablet comprising: (a) a core comprising deferiprone in an amount of about 85.0% to about 95.0% by weight of the tablet, a modifying release agent comprising glyceryl esters of long fatty acids in an amount of about 1.0% to about 2.0% by weight of the tablet, a lubricant and/or glidant in an amount of about 0 to about 2.0% by weight of the tablet, and additional pharmaceutically acceptable excipients in an amount of about 0 to about 13.0% by weight of the tablet; and (b) an enteric coating; wherein the tablet is suitable for twice a day oral administration. In some aspects, the modifying release agent is present in an amount of about 1.5% by weight of the tablet.

In some aspects is provided a modified release enteric coated pharmaceutical formulation for twice-a-day oral administration, wherein the pharmaceutical formulation is a tablet, and wherein the core of the tablet comprises deferiprone in an amount of about 85 to 95%, glyceryl esters of long fatty acids as a modified release agent in an amount of about 1.0 and 2.0%, optionally in an amount of about 1.5%, a lubricant and/or glidant in an amount of about 0 to 2.0%, and other suitable pharmaceutically acceptable excipients in an amount of about 0 to 13.0%, wherein all the amounts calculated by weight on the total weight of the formulation.

In some aspects, the ratio of deferiprone to the modifying release agent (i.e., glyceryl esters of long fatty acids or mixtures thereof) is from about 99:1 to about 98:2.

In some aspects, the deferiprone is present in the core in an amount of about 75.0% to about 98.0% by weight of the tablet. In some aspects, the deferiprone is present in the core in an amount of about 75.0% to about 95.0% by weight of the tablet. In some aspects, the deferiprone is present in the core in an amount of about 80.0% to about 95.0% by weight of the tablet. In some aspects, the deferiprone is present in the core in an amount of about 85.0% to about 95.0% by weight of the tablet. In some aspects, the deferiprone is present in the core in an amount of about 85.0%, or about 86.0%, or about 87.0%, or about 88.0%, or about 89.0%, or about 90.0%, or about 91.0%, or about 92.0%, or about 93.0%, or about 94.0%, or about 95.0% by weight of the tablet.

In some aspects, the deferiprone is present in the core in an amount of about 400 mg to about 2000 mg. In some aspects, the deferiprone is present in the core in an amount of about 500 mg to about 1500 mg. In some aspects, the deferiprone is present in the core in an amount of about 600 mg to about 1400 mg. In some aspects, the deferiprone is present in the core in an amount of about 700 mg to about 1300 mg. In some aspects, the deferiprone is present in the core in an amount of about 800 mg to about 1200 mg. In some aspects, the deferiprone is present in the core in an amount of about 900 mg to about 1100 mg. In some aspects, the deferiprone is present in the core in an amount of about 500 mg, or about 600 mg, or about 700 mg, or about 800 mg, or about 900 mg, or about 1000 mg, or about 1100 mg, or about 1200 mg, or about 1300 mg, or about 1400 mg, or about 1500 mg. In some aspects, the deferiprone is present in the core in an amount of about 1000 mg.

In some aspects, the modifying release agent is present in an amount of about 0.5% to about 8.0% by weight of the tablet. In some aspects, the modifying release agent is present in an amount of about 0.5% to about 6.0% by weight of the tablet. In some aspects, the modifying release agent is present in an amount of about 0.5% to about 4.0% by weight of the tablet. In some aspects, the modifying release agent is present in an amount of about 0.5% to about 3.0% by weight of the tablet. In some aspects, the modifying release agent is present in an amount of about 1.0% to about 2.0% by weight of the tablet. In some aspects, the modifying release agent is present in an amount of about 0.5% by weight, or about 1.0% by weight, or about 1.5% by weight, or about 2.0% by weight, or about 2.5% by weight, or about 3.0% by weight of the tablet. In some aspects, the modifying release agent is present in an amount of about 1.0% by weight of the tablet. In some aspects, the modifying release agent is present in an amount of about 1.5% by weight of the tablet. In some aspects, the modifying release agent is present in an amount of about 2.0% by weight of the tablet.

In some aspects, the modifying release agent is selected from the group consisting of glyceryl palmitostearate, glyceryl monostearate, glyceryl dibehenate, and combinations thereof. In some aspects, the modifying release agent is glyceryl dibehenate. In some aspects, the modifying release agent is glyceryl palmitostearate. In some aspects, the modifying release agent is glyceryl monostearate. In some aspects, the modifying release agent is a combination of glyceryl palmitostearate, glyceryl monostearate, and glyceryl dibehenate. In some aspects, the modifying release agent is a combination of glyceryl palmitostearate and glyceryl monostearate. In some aspects, the modifying release agent is a combination of glyceryl palmitostearate and glyceryl dibehenate. In some aspects, the modifying release agent is a combination of glyceryl monostearate and glyceryl dibehenate.

In another aspect is provided a modified release tablet comprising: (a) a core comprising deferiprone in an amount of about 85.0% to about 88.0% by weight of the tablet, a modifying release agent comprising glyceryl esters of long fatty acids in an amount of about 8.0% and about 15.0% by weight of the tablet, a lubricant and/or glidant in an amount from about 0 to about 2.0% by weight of the tablet, and additional pharmaceutically acceptable excipients in an amount of about 0 to about 5.0% by weight of the tablet; and (b) an enteric coating; wherein the tablet is suitable for once a day oral administration.

In some aspects is provided a modified release enteric coated pharmaceutical formulation for once-a-day oral administration, wherein the pharmaceutical formulation is a tablet, and wherein the core of the tablet comprises deferiprone in an amount of about 85 to 88%, glyceryl esters of long fatty acids as a modified release agent in an amount of about 8.0 and 15.0%, a lubricant and/or glidant in an amount of about 0 to 2.0%, and optionally other suitable pharmaceutically acceptable excipients in an amount of about 0 to 5.0%, wherein all the amounts calculated by weight on the total weight of the formulation.

In some aspects, the ratio of deferiprone to the modifying release agent (i.e., glyceryl esters of long fatty acids or mixtures thereof) is from about 90:10 to about 85:15.

In some aspects, the deferiprone is present in the core in an amount of about 75.0% to about 95.0% by weight of the tablet. In some aspects, the deferiprone is present in the core in an amount of about 80.0% to about 90.0% by weight of the tablet. In some aspects, the deferiprone is present in the core in an amount of about 82.0% to about 88.0% by weight of the tablet. In some aspects, the deferiprone is present in the core in an amount of about 85.0% to about 88.0% by weight of the tablet. In some aspects, the deferiprone is present in the core in an amount of about 82.0%, or about 83.0%, or about 84.0%, or about 85.0%, or about 86.0%, or about 87.0%, or about 88.0%, or about 89.0%, or about 90.0% by weight of the tablet.

In some aspects, the deferiprone is present in the core in an amount of about 400 mg to about 2000 mg. In some aspects, the deferiprone is present in the core in an amount of about 500 mg to about 1500 mg. In some aspects, the deferiprone is present in the core in an amount of about 600 mg to about 1400 mg. In some aspects, the deferiprone is present in the core in an amount of about 700 mg to about 1300 mg. In some aspects, the deferiprone is present in the core in an amount of about 800 mg to about 1200 mg. In some aspects, the deferiprone is present in the core in an amount of about 900 mg to about 1100 mg. In some aspects, the deferiprone is present in the core in an amount of about 500 mg, or about 600 mg, or about 700 mg, or about 800 mg, or about 900 mg, or about 1000 mg, or about 1100 mg, or about 1200 mg, or about 1300 mg, or about 1400 mg, or about 1500 mg. In some aspects, the deferiprone is present in the core in an amount of about 1000 mg.

In some aspects, the modifying release agent is present in an amount of about 2.0% to about 20.0% by weight of the tablet. In some aspects, the modifying release agent is present in an amount of about 5.0% to about 18.0% by weight of the tablet. In some aspects, the modifying release agent is present in an amount of about 8.0% to about 15.0% by weight of the tablet. In some aspects, the modifying release agent is present in an amount of about 10.0% to about 12.0% by weight of the tablet. In some aspects, the modifying release agent is present in an amount of about 7.0% by weight, or about 8.0% by weight, or about 9.0% by weight, or about 10.0% by weight, or about 11.0% by weight, or about 12.0% by weight, or about 13.0% by weight, or about 14.0% by weight, or about 15.0% by weight, or about 16.0% by weight of the tablet. In some aspects, the modifying release agent is present in an amount of about 8.0% by weight of the tablet. In some aspects, the modifying release agent is present in an amount of about 10.0% by weight of the tablet. In some aspects, the modifying release agent is present in an amount of about 12.0% by weight of the tablet. In some aspects, the modifying release agent is present in an amount of about 15.0% by weight of the tablet.

In some aspects, the modifying release agent is selected from the group consisting of glyceryl palmitostearate, glyceryl monostearate, glyceryl dibehenate, and combinations thereof. In some aspects, the modifying release agent is glyceryl dibehenate. In some aspects, the modifying release agent is glyceryl palmitostearate. In some aspects, the modifying release agent is glyceryl monostearate. In some aspects, the modifying release agent is a combination of glyceryl palmitostearate, glyceryl monostearate, and glyceryl dibehenate. In some aspects, the modifying release agent is a combination of glyceryl palmitostearate and glyceryl monostearate. In some aspects, the modifying release agent is a combination of glyceryl palmitostearate and glyceryl dibehenate. In some aspects, the modifying release agent is a combination of glyceryl monostearate and glyceryl dibehenate.

In some aspects, the enteric coating comprises enteric polymers. In some aspects, the enteric polymers for the enteric coating include, e.g., hydroxypropyl methylcellulose acetate succinate (also referred to as hypromellose acetate succinate or HPMCAS), HPMC phthalate (also referred to as hypromellose phthalate), polyvinyl acetate phthalate, cellulose acetate phthalate, cellulose acetate trimellitate, shellac, zein, methacrylic acid copolymers (e.g., methacrylic acid copolymer Type C Dispersion 30%), derivatives thereof, and combinations thereof.

In some aspects, the enteric polymers in the enteric coating are HPMC acetate succinate and methacrylic acid copolymers, e.g., methacrylic acid copolymer type C in aqueous dispersion.

In some aspects, the enteric polymer in the coating is about 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.5%, 3%, 3.5%, or 4%, by weight of the tablet, or a range between any two of the preceding values, e.g., 0.5-1%, 0.5-2%, 0.5-3%, 0.5-4%, 0.6-1%, 0.6-2%, 0.6-3%, 0.6-4%, 0.7-1%, 0.7-2%, 0.7-3%, 0.7-4%, 1-1.5%, 1.1-1.7%, 1-2%, 1.5-2%, 1-3%, 1-3.5%, or 1-4%, by weight of the tablet. In some aspects, the enteric polymer in the coating (e.g., methacrylic acid copolymer) is about 0.8% by weight of tablet. In some aspects, the enteric polymer in the coating (e.g., methacrylic acid copolymer) is about 1.4% by weight of the tablet (e.g., methacrylic acid copolymer).

In some aspects, the enteric coating comprises about 5 mg, 5.5 mg, 6 mg, 6.5 mg, 7 mg, 7.5 mg, 8 mg, 8.5 mg, 9 mg, 9.5 mg, 10 mg, 11 mg, 12 mg, 13 mg, 14 mg, 15 mg, 16 mg, 17 mg, 18 mg, 19 mg, 20 mg, 25 mg, or 30 mg of an enteric polymer, or a range between any two of the preceding values, e.g. about 5-20 mg, 7-20 mg, 7-30 mg, 8-15 mg, or 8-10 mg of an enteric polymer.

In some aspects, the enteric coating comprises, in addition to the enteric polymer, other excipients, including for example, a plasticizer, a lubricant or anti-tack agent such as talc, an opacifier, a colorant, a diluent, or any combination thereof.

In some aspects, the plasticizer is diethyl phthalate, citrate esters such as triethyl citrate, polyethylene glycol, glycerol, acetylated glycerides, acetylated citrate esters, dibutyl sebecate, castor oil, or any combination thereof.

In some aspects, the enteric coating comprises about 0.5 mg, 0.6 mg, 0.7 mg, 0.8 mg, 0.9 mg, 1 mg, 1.1 mg, 1.2 mg, 1.3 mg, 1.4 mg, 1.5 mg, 2 mg, 2.5 mg, 3 mg, 3.5 mg, 4 mg, 4.5 mg, or 5 mg of a plasticizer, or a range between any two of the preceding values, e.g. about 0.5-5 mg, 0.7-2 mg, or 0.8-1.2 mg of a plasticizer.

In some aspects, the enteric coating may further comprise a diluent (e.g., lactose, sucrose, fructose, mannitol, and the like, or combinations thereof). In some aspects, the enteric coating comprises talc as the lubricant or anti-tack agent.

In some aspects, the enteric coating comprises triethyl citrate, talc, titanium dioxide, and a methacrylic acid copolymer dispersion.

In some aspects, the enteric coating comprises a methacrylic acid copolymer dispersion. In some aspects, the enteric coating comprises an ethacrylic acid-ethyl acrylate copolymer (1:1) dispersion in water and propylene glycol. The ethacrylic acid-ethyl acrylate copolymer (1:1) is available as Eudragit® L30-D55 from Evonik Operations GmbH, Essen Germany.

In some aspects, the enteric coating comprises methacrylic acid-methacrylate copolymer (1:1) in an alcoholic solution. In some aspects, the methacrylic acid-methacrylate copolymer (1:1) is present in a concentration of 5-15% w/w, or 10% w/w, with triethyl citrate as plasticizer. In some aspects, the triethyl citrate is present in a concentration in relation to the polymer of 2-5% w/w, or 3% w/w.

Methacrylic acid-methacrylate copolymer (1:1) is available as Eudragit® L100 (dissolution pH around 6.8) from Sigma-Aldrich (Missouri, USA).

In some aspects, the enteric coating can be applied according to methods known to the skilled person. In some aspects, the enteric coating can be applied over 15 to 20 minutes.

In some aspects, the core may comprise one or more pharmaceutically acceptable excipients such as bulking agents and/or basic excipient.

Advantageously, the bulking agent when present can increase tablet hardness. In some aspects, the bulking agent is selected from the group consisting of calcium carbonate, dibasic calcium phosphate, tribasic calcium phosphate, calcium sulfate, microcrystalline cellulose, powdered cellulose, dextrans, dextrin, dextrose, fructose, kaolin, lactose, mannitol, sorbitol, starch, pregelatinized starch, sucrose, alpha-lactose monohydrate.

In some aspects, the basic excipient is selected from the group consisting of meglumine, metal oxides, metal hydroxides, basic salts of weak acids, and a combination thereof. Metal oxides include, but are not limited to, magnesium oxide, aluminum oxide, and zinc oxide. Metal hydroxides include, but are not limited to, sodium hydroxide, potassium hydroxide, magnesium hydroxide, and calcium hydroxide. Basic salts of weak acids include, but are not limited to, sodium or potassium salts of carbonate, bicarbonate, acetate, and citrate. In some aspects, the basic excipient is magnesium oxide, meglumine or a combination thereof. In some aspects, the basic excipient is magnesium oxide.

In some aspects, the modified release tablets comprise a lubricant to prevent sticking to the tooling during compression into tablets, and/or a glidant to improve flow in the tableting process, or combinations thereof.

In some aspects, the lubricant is selected from the group consisting of, but not limited to, magnesium stearate, calcium stearate, stearic acid, sodium stearyl fumarate, or combination thereof in amount comprised between 0.1 and 1.0% by weight.

In some aspects, the lubricant is selected is selected from the group consisting of magnesium stearate, calcium stearate, stearic acid, sodium stearyl fumarate, talc, and a combination thereof.

In some aspects, the lubricant is magnesium stearate. In some aspects, the glidant is selected from the group consisting of, but not limited to, colloidal silicon dioxide, starch and talc, preferably colloidal silicon dioxide or combination thereof.

In some aspects, the core of modified release tablet comprises a mixture of magnesium stearate and colloidal silicon dioxide.

In some aspects, the lubricant and/or glidant is present in an amount from about 0 to about 5.0% by weight of the tablet. In some aspects, the lubricant is present in an amount from about 0 to about 4.0% by weight of the tablet. In some aspects, the lubricant is present in an amount from about 0 to about 3.0% by weight of the tablet. In some aspects, the lubricant is present in an amount from about 0 to about 2.0% by weight of the tablet. In some aspects, the lubricant is present in an amount of about 0.5% by weight of the tablet. In some aspects, the lubricant is present in an amount of about 1.0% by weight of the tablet. In some aspects, the lubricant is present in an amount of about 1.5% by weight of the tablet. In some aspects, the lubricant is present in an amount of about 2.0% by weight of the tablet. In some aspects, the lubricant is present in an amount of about 2.5% by weight of the tablet. In some aspects, the lubricant is present in an amount of about 3.0% by weight of the tablet.

In some aspects, the core comprises:
i) deferiprone in an amount of 90.9% by weight; glyceryl behenate in an amount of 1.5% by weight; a pH adjusting agent in an amount of 0.5% by weight of the tablet;
ii) a bulking agent in an amount of 6.9% by weight of the tablet;
iii) a mixture of a lubricant and glidant in an amount of 0.2% by weight of the tablet.

In some aspects, the core comprises:
i) deferiprone in an amount of 90.7% by weight of the tablet;
ii) glyceryl behenate in an amount of 9.1% by weight of the tablet;
iii) a mixture of a lubricant and glidant in an amount of 0.2% by weight of the tablet.

In some aspects, the core of the modified release tablet may only consist of deferiprone and glyceryl behenate.

In some aspects, the core comprises:
i) deferiprone in an amount between 98.0% and 99.0% by weight of the tablet; and
ii) glyceryl behenate in an amount between 1.0% and 2.0% by weight of the tablet.

In some aspects, the core comprises:
i) deferiprone in an amount between 80.0% and 90.0% by weight of the tablet; and
ii) glyceryl behenate in an amount between 10.0% and 20.0% by weight of the tablet.

It has been found that glyceryl behenate, due to its squeezing out properties, may act as a lubricant, so other lubricants to improve tabletting might not be needed. Thus, in some aspects, the modified release tablet comprises glyceryl behenate as the modifying release agent and does not contain any other lubricants.

Furthermore, by using a hydrophobic excipient such as glyceryl behenate, which is insensitive to pH variation, the formulation would be less influenced by the external environment that the formulation has to face during transit along the regions in which the release of the active agent takes place, which are characterized by physiological fluids having different pH's. Hence, the release can be more predictable because it is no longer at the mercy of random microenvironmental variation of the pH.

This is a particular benefit during the transit in the stomach of fed subjects, wherein random microenvironmental variation of the pH occur more frequently.

Advantageously, the tablets as disclosed herein are debossed with a score line, to make it easy for the patient to break the tablets into two approximately equal parts to enable administration of half tablets, allowing a dosing flexibility.

Needless-to-say, it is difficult to combine both features into a single tablet; that is, to produce a tablet that is enteric coated but can be broken into two parts without destroying the delayed release feature. This is because the surface at the interface of a broken tablet is no longer protected by the enteric coating.

If the unprotected core disintegrates and/or dissolves quickly, the dissolution of the broken tablet in the stomach acid will be faster than the whole tablet, so that protection against gastric irritation will be partially lost and the broken tablet no longer delivers the drug at the same rate and possibly of the whole tablet.

On the other hand, as long as said dissolution is around 20% at acidic pH, or below this value, this is considered acceptable.

Figure 4:
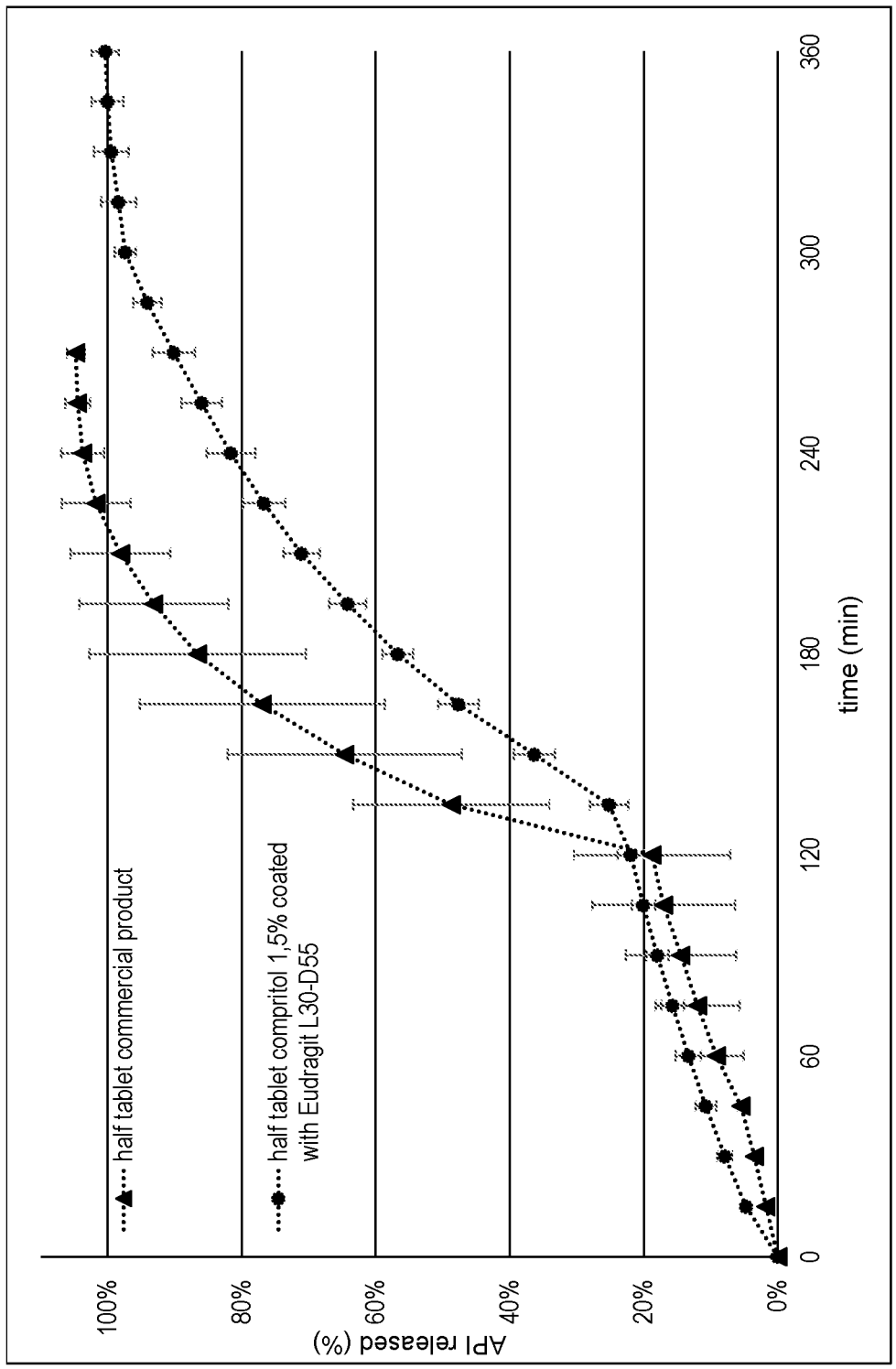
FIG. 4—Dissolution tests of the half-coated tablets comprising glyceryl esters of behenic acid (e.g., Compritol®) 1.5% in 900 ml of pH 1.2 medium (120 min) and then pH 6.8 medium, basket (apparatus 1) having rotational speed of 100 rpm. The line with a triangular indicator is referred to the commercial product.

As a further advantage, as reported in FIG. 4, although the release is a bit higher at low pH than the commercial tablets, the half tablets as disclosed herein, when a change of the pH occurs, do not show any undesired burst effect, and exhibit a smoother release of the active agent in the first phase of the dissolution.

In fact, it is well known that transient higher concentrations and hence plasma levels of deferiprone, could be associated with transient increase of liver enzymes and other side effects (Cohen E R et al Br J Haematology, 2000, 108, 305-312)

Accordingly, the tablet could be administered as a whole tablet, otherwise the tablet could be scored for administration of about half the dosage of the whole tablet.

Advantageously, a tablet of the present disclosure comprising a low amount of the matrix embraces the attributes of an enteric coated tablet suitable for twice-a-day administration, without its deficiencies, so that tablets can be halved, to enable fine tuning of the dosing to administer whole tablets, half tablets, or any combination thereof. Half tablets of the disclosure substantially resist dissolution in acidic media (0.1 N HCl), representing the fasted stomach contents, as do whole tablets; and, at a higher pH, representing the contents of the small intestine, also exhibit a rate of dissolution similar to whole tablets, but without the undesired burst effect of the reference product on the market.

In another aspects, a tablet of the present disclosure comprising a higher amount of the matrix embraces the attributes of an enteric coated tablet suitable for once-a-day administration.

The release profile of the modified release tablets as disclosed herein has been determined in different dissolution media varying the pH according to the conditions reported in Example 2.

In some aspects, the modified release tablets disclosed herein containing glyceryl behenate, e.g., in an amount of about 1.0-2.0%, give rise to a dissolution profile at pH 6.8 similar to that of Ferriprox® tablets as approved by FDA and sold in the United States. In some aspects, the modified release tablets show the same bioavailability at the steady state, making it suitable for a twice a day oral administration.

In some aspects, the modified release tablet formulation is bioequivalent in the steady state to the immediate release Ferriprox® tablets for three times a day administration, the mean ratio of AUC (over 24 hours) and the mean ratio of Cmax for the tablets of the disclosure relative to the immediate release (IR) tablets would be within 80% to 125%.

In some aspects, in the steady state, the disclosed modified release tablets comprising a lower amount of glyceryl behenate when administered twice-a-day would be able to achieve the same maximum peak concentrations ($C_{max}$) as IR tablets of Ferriprox®, when the IR tablets were given three times a day, and the total amount absorbed (AUC) would be the same for both products over a 24-hour period.

In contrast, the disclosed modified release tablets containing a higher amount of glyceryl behenate, i.e 8.0-15% give rise to a slower dissolution profile that could make them suitable for a once-a-day oral administration.

This would improve the compliance of the patients and their therapeutic regimen adherence, as well as improving safety and causing less gastrointestinal distress, without a compromise on efficacy.

In some aspects, as a result of the dissolution test, a pH 4.5 or a pH 6.8 the disclosed modified release tablet for once-a-day administration releases less than 20% w/w of the active ingredient within 1.0 hours, less than 40% w/w within 3 hours, and less than 50% within 6 hours when subjected to a dissolution test at a pH of 4.5 or a pH of 6.8.

Methods of Preparation

In another aspect is provided a process for the preparation of the modified release tablet as disclosed herein, said process comprising:
i) mixing deferiprone with the modifying release agent and the pharmaceutically acceptable excipients, if present to form a mixture;
ii) wet-granulating the mixture obtained in step (i) in a high shear granulator followed by drying and screening to produce a granulate;
iii) mixing the granulate obtained in step (ii) with the lubricant/glidant to form a mixture;
iv) compressing the mixture obtained in step (iii) to form a tablet;
v) and coating the tablet.

In another aspect is provided a process for the preparation of the modified release tablet as disclosed herein, said process comprising:
  i) mixing deferiprone with the modifying release agent and the pharmaceutically acceptable excipients, if present;
  ii) adding the lubricant/glidant and further mixing to form a mixture;
  iii) directly compressing the mixture obtained in step (iii) to form a tablet; and
  iv) coating the tablet.

Apparatus and conditions for direct compression and/or compression upon granulation are known to the skilled person in the art.

The modified release tablets could be prepared in any suitable weight. In some aspects, the tablets are prepared in a weight of about 500 mg to about 2500 mg. In some aspects, the tablets are prepared in a weight of about 600 mg to about 2000 mg. In some aspects, the tablets are prepared in a weight of about 800 mg to about 1500 mg. In some aspects, the tablets are prepared in a weight of about 1000 mg to about 1200 mg.

Other pharmaceutically acceptable excipients and procedures mentioned herein can be found in, for example, Handbook of Pharmaceutical Excipients, Third Edition, edited by Arthur H. Kibbe, American Pharmaceutical Association, Washington, USA and Pharmaceutical Press, London; and Lexikon der Hilfsstoffe fi.ir Pharmazie, Kosmetik and angrenzende Gebiete edited by H. P. Fiedler, 4th Edition, Editor Cantar, Aulendorf and earlier editions.

In some aspects, the modified release tablet can be administered to patients using dosing regimens useful for the therapeutic use of the pharmaceutical formulations described herein In some aspects, the oral daily dose with food of deferiprone could range from 75 mg/kg to 100 mg/kg.

In some aspects, the modified release tablet is administered to a subject in need thereof twice daily. In some aspects, the modified release tablet is administered once daily.

In some aspects, the unit dose of deferiprone in the modified release tablets shall be comprised between 500 and 1500 mg, or between 600 and 1000 mg, depending on the frequency of administration.

Methods of Treatment

The claimed formulations are useful for the treatment of diseases which cause an overload of iron, or for the prevention and/or treatment of diseases which are caused by an overload of iron In some aspects, the subject in need thereof suffers from iron overload due to transfusional iron overload, or due diseases such as thalassemia, myelodysplasia, or sickle cell disease.

In some aspects, the subject in need thereof suffers from a neurodegenerative disease (e.g., Parkinson's disease, amyotrophic lateral sclerosis (ALS), Huntington's disease, Friedreich's Ataxia, Pantothenate Kinase Associated Neurodegeneration (PKAN), or neurodegeneration with brain iron accumulation (NBIA).

In some aspects, the subject in need thereof suffers from iron overload that is transfusional iron overload. In certain aspects, the subject suffers from transfusional iron overload and whose prior chelation therapy is inadequate. In certain aspects, the subject suffers from transfusion iron overload and has a cardiac MRI T2* of 20 ms or less (e.g., 10 ms).

In another aspect is provided the modified release tablet as described herein for use in the treatment of diseases which cause an overload of iron, or for the prevention and/or treatment of diseases which are caused by an overload of iron. In some aspects, the disease is thalassemia or sickle cell anemia. In some aspects, the iron overload is transfusional iron overload.

In another aspect is provided a method of treating a disease which causes an overload of iron, comprising administering the modified release tablet as described herein. In some aspects, the disease is thalassemia or sickle cell anemia. In some aspects, the iron overload is transfusional iron overload.

In another aspect is provided a method of treating and/or preventing a disease which is caused by an overload of iron, comprising administering the modified release tablet as described herein. In some aspects, the iron overload is transfusional iron overload.

In another aspect is provided the modified release tablet as described herein for the manufacture of a medicament for the treatment of diseases which cause an overload of iron, or for the prevention and/or treatment of diseases which are caused by an overload of iron. In some aspects, the disease is thalassemia or sickle cell anemia. In some aspects, the iron overload is transfusional iron overload.

In another aspect is provided a method for reducing gastric distress or the risk of gastric distress in a patient in need of deferiprone treatment, comprising orally administering to the patient a modified release tablet comprising: (a) a core comprising deferiprone in an amount of about 85.0% to about 88.0% by weight of the tablet, a modifying release agent comprising glyceryl esters of long fatty acids in an amount of about 8.0% and about 15.0% by weight of the tablet, a lubricant and/or glidant in an amount from about 0 to about 2.0% by weight of the tablet, and additional pharmaceutically acceptable excipients in an amount of about 0 to about 5.0% by weight of the tablet; and (b) an enteric coating; wherein the tablet is suitable for once a day oral administration.

In another aspect is provided a method for reducing gastric distress or the risk of gastric distress in a patient in need of deferiprone treatment, comprising orally administering to the patient a modified release enteric coated pharmaceutical formulation, wherein the pharmaceutical formulation is a tablet, and wherein the core of the tablet comprises deferiprone in an amount of about 85 to 88%, glyceryl esters of long fatty acids or mixture thereof as a modified release agent in an amount of about 8.0 and 15.0%, a lubricant and/or glidant in an amount of about 0 to 2% optionally, and other suitable pharmaceutically acceptable excipients in an amount of about 0 to 5%, wherein all the amounts calculated by weight on the total weight of the formulation, and wherein the formulation is suitable for once daily dosing.

Because the administration of a modified release tablet suitable for once a day oral administration is less frequent, it is believed that the gastric distress of the patient is reduced as compared to orally administering an immediate release formulation and/or a twice-a-day formulation, with an advantage for the comfort of the patient.

The disclosure is illustrated in detail by the following examples.

EXAMPLES

Example 1—Preparation of the Tablets

Tablets were prepared by direct compression using a rotary tablet press (Officine Meccaniche Ronchi, AM8S) equipped with oblong punches having dimensions of 22 mm×10 mm. Compression force was set at 25 kN in order to have tablets with a crushing strength of about 70 N.

The composition of tablets containing 1000 mg of active and Compritol® 888 ATO (Gattefossé SAS) in different percentages is reported in Table 1.

TABLE 1

Formulations of oblong tablets formulated with inert excipient Compritol 888 ATO

| MATRIX NAME | API (mg) | Compritol ® 888 ATO (mg) |
|---|---|---|
| TC 1.5% | 1000 | 15 |
| TC 3% | 1000 | 30 |
| TC 5% | 1000 | 50 |
| TC 10% | 1000 | 100 |

The release profiles acquired in different dissolution media

Example 2—Dissolution Test

The spectrum of maximum absorption of the active was acquired in the various fluids in which the release tests will be conducted by means of a spectrophotometer.

Compositions of dissolution media are reported below.
pH 1.2: for 1 L, 3.73 g KCl, 7.07 ml HCl 1N (deionized water up to volume) pH 4.5: for 1 L, 6.80 g of $KH_2PO_4$ (deionized water up to volume)
pH 6.8: for 1 L, 6.80 g $KH_2PO_4$, 0.90 g of NaOH (deionized water up to volume)

Calibration curves were built for each of the release media both at the wavelength of 276 nm at which a peak of absorbance was recorded, and at 243 nm, in which reduced absorption was observed, in order not to exceed the instrument maximum absorbance value.

The release test of the commercial product was analyzed at the wavelength of 276 nm both in pH 4.5 phosphate, and with the pH change mode (HCl 0.1 N for the first 120 minutes and phosphate buffer pH 6.8 for the remainder of the test). At high values of absorbance (over 30% of the release) sampling, dilutions and manual readings was performed.

Release tests were carried out in a dissolution test paddle apparatus (USP type 2) with a rotation speed of 50 rpm and basket apparatus (USP type 1) with a rotation speed of 100 rpm [FIG. 4]. The tests were always conducted in 900 mL of dissolution medium at 37° C.

For the experimental formulations, the active ingredient was quantified by spectrophotometry at a wavelength of 24.3 nm.

Figure 2:
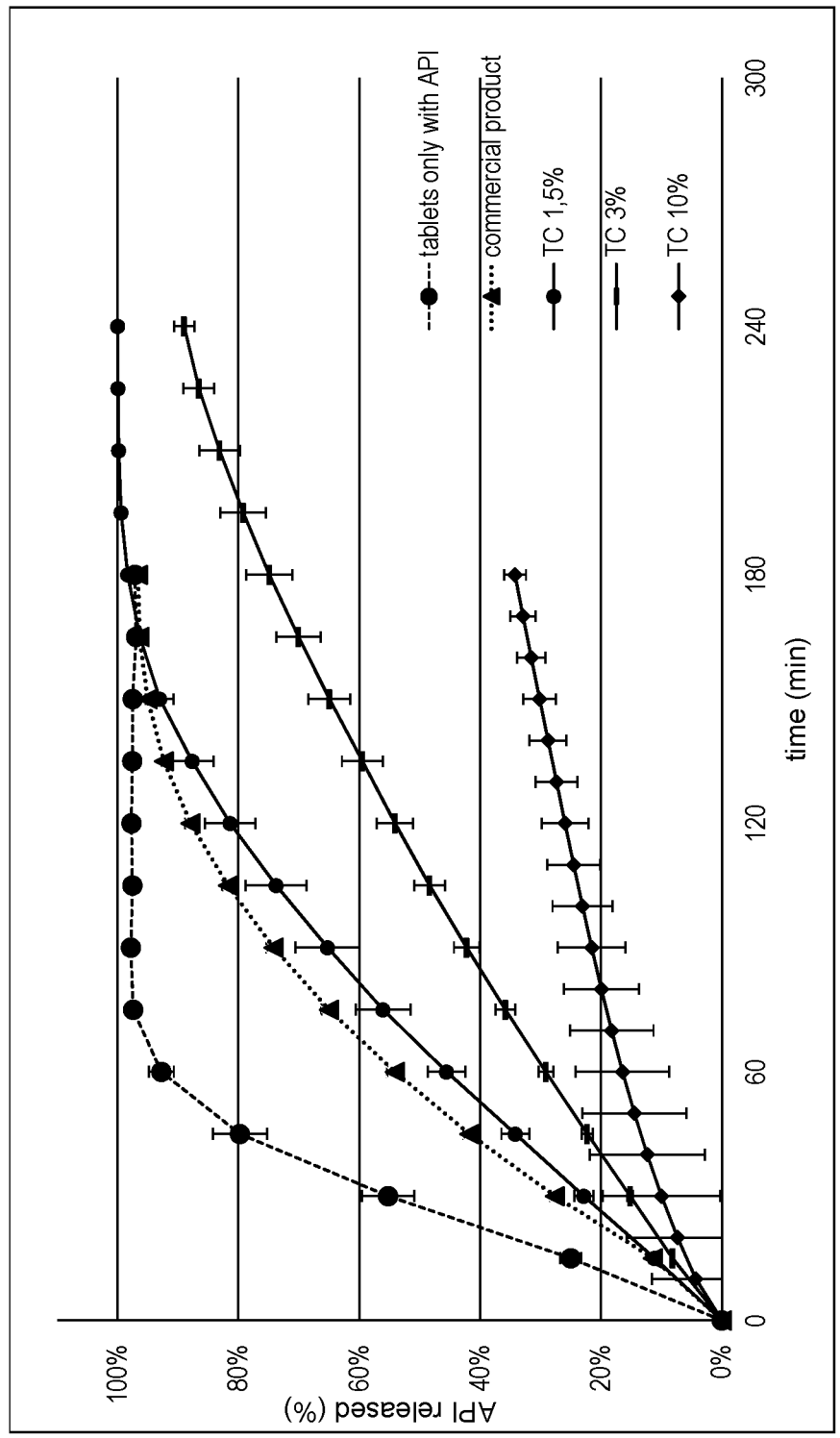
FIG. 2: Dissolution tests of glyceryl esters of behenic acid (e.g., Compritol®) formulations carried out in 900 ml of pH 4.5 medium, paddle (apparatus 2) having rotational speed of 50 rpm. The line with a triangular indicator is referred to the commercial product.

The release profiles acquired in different dissolution media at pH 6.8 and 4.5 are reported in FIGS. 1 and 2.

As it can be appreciated, using different % of Compritol® 888 ATO as a matrix different release profiles are obtained.

In particular with an amount of 1.5% by weight, a formulation could be prepared having a release profile similar to the reference product, and hence suitable for twice a day administration.

On the contrary, using an amount of 10% by weight, the dissolution dramatically slows down and an in vitro profile potentially suitable for once-a-day administration is obtained.

The coated tablets confirm the above findings.

Example 3—Gastroresistant Coating

Tablets comprising Compritol® 888 ATO 1.5% were coated with an acrylic polymer having a dissolution pH around 6 and formulated in aqueous dispersion:

Eudragit® L30-D55 aqueous dispersion 60% w/w (containing 25% solids)
Deionized water 38% w/w
Propylene glycol 2% w/w
Process parameters were the followings:
Nozzle: 0.8 mm
Atomization pressure: 0.8 bar
Control pressure: 2 bar
Pattern pressure: 0.5 bar
Peristaltic pump: 2 rpm
Air temperature: 57° C.

Coating process lasted for 20 minutes and samples were subjected to dissolution test.

Said tests have been conducted at 37° in Apparatus 1 (basket) with a rotational speed of 100 rpm in the following dissolution media:
pH 1.2 (for 1 L, 3.73 g KCl, 7.07 mL HCl 1N and deionized water up to volume) for the first 120 minutes
pH 6.8 (for 1 L, 6.80 g $KH_2PO_4$, 0.90 g of NaOH and deionized water up to volume) for the rest of the dissolution time.

Figure 3:
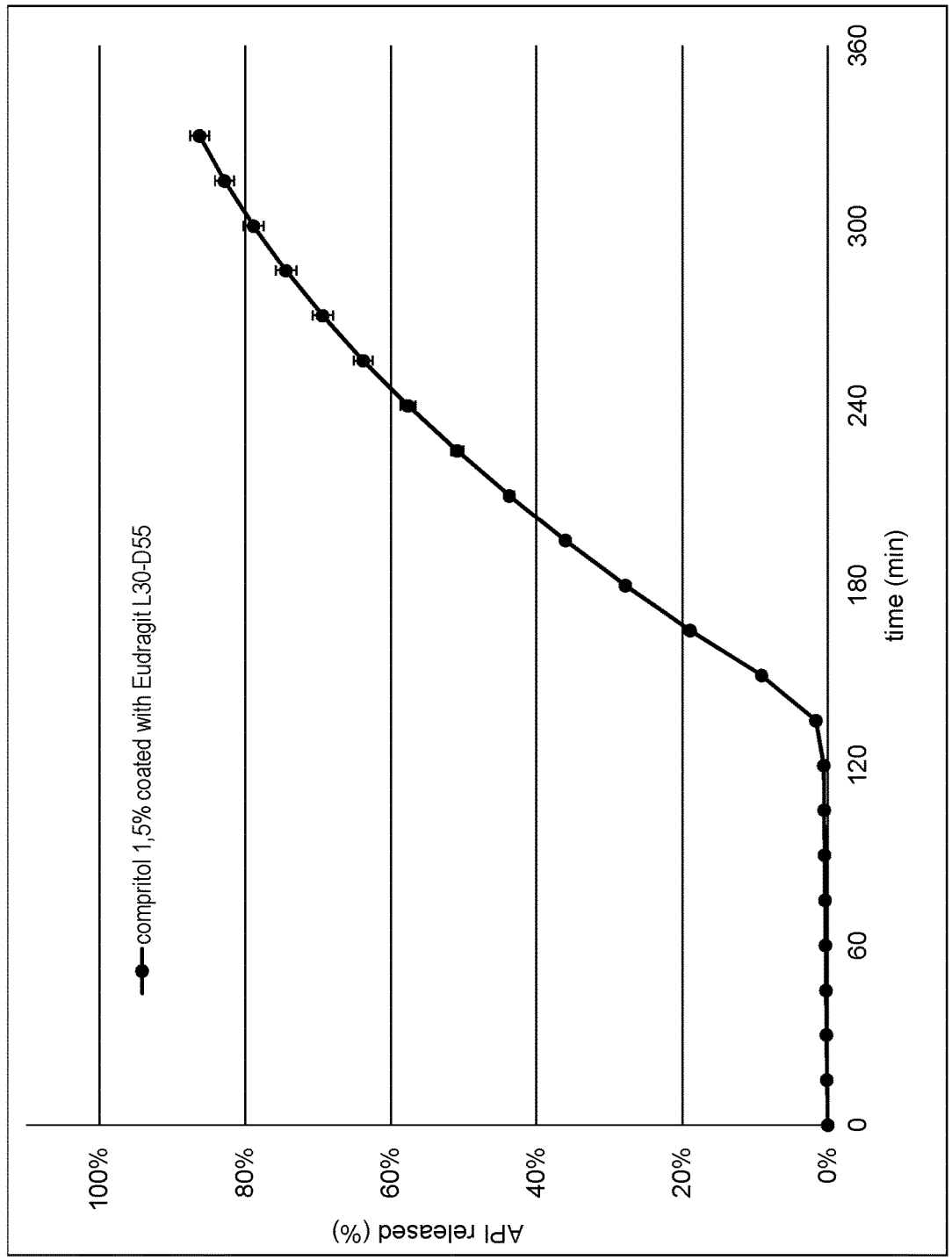
FIG. 3—Dissolution tests of the coated tablets comprising glyceryl esters of behenic acid (e.g., Compritol®) 1.5% carried out in 900 ml of pH 1.2 medium (120 min) and then pH 6.8 medium, basket (apparatus 1) having rotational speed of 100 rpm.

The results for the whole tablets are reported in FIGS. 3 and 4, respectively.

As it can be appreciated from FIG. 3, the release of the coated tablets is negligible until a change of the pH occurs, then a curve similar to the one reported in Figure is observed for deferiprone, confirming that said profile would be suitable for twice-a-day administration From FIG. 4 concerning the half tablets, it could be observed that, although the release of the active ingredient is a bit higher at low pH than the commercial tablets, the half tablets as disclosed herein, when a change of the pH occurs, do not show any undesired burst effect, with a smoother release of the active ingredient in the first phase of the dissolution.

In addition to the various aspects described herein, the present disclosure includes the following aspects numbered A1 through A23. This list of aspects is presented as an exemplary list and the application is not limited to these aspects.

A1. A pharmaceutical formulation comprising deferiprone and a modifying release agent comprising glyceryl esters of long fatty acids, wherein said pharmaceutical formulation is suitable for twice-a-day or once-a-day oral administration.

A2. The pharmaceutical formulation according to A1, which is in form of gastroresistant capsules, enteric coated capsules, or enteric coated modified release tablets.

A3. The modified release tablet according to A2, wherein the modifying release agent is selected from the group consisting of glyceryl palmitostearate, glyceryl monostearate, glyceryl dibehenate, and combinations thereof.

A4. The modified release tablet according to A2 or A3, wherein the modifying release agent is glyceryl dibehenate.

A5. A modified release tablet comprising: (a) a core comprising deferiprone in an amount of about 85.0% to about 95.0%% by weight of the tablet, a modifying release agent comprising glyceryl esters of long fatty acids in an amount of about 1.0% to about 2.0% by weight of the tablet, a lubricant and/or glidant in an amount of about 0 to about 2.0% by weight of the tablet, and additional pharmaceutically acceptable excipients in an amount of about 0 to 13.0% by weight of the tablet; and (b) an enteric coating; wherein the tablet is suitable for twice a day oral administration.

A6. A modified release tablet comprising: (a) a core comprising deferiprone in an amount of about 85.0% to about 88.0% by weight of the tablet, a modifying release agent comprising glyceryl esters of long fatty acids in an amount of about 8.0% and about 15.0% by weight of the tablet, a lubricant and/or glidant in an amount from about 0 to about 2.0% by weight of the tablet, and additional pharmaceutically acceptable excipients in an amount of about 0 to about 5.0% by weight of the tablet; and (b) an enteric coating; wherein the tablet is suitable for once a day oral administration.

A7. The modified release tablet according to A5 or A6, wherein the modifying release agent is selected from the group consisting of glyceryl palmitostearate, glyceryl monostearate, glyceryl dibehenate, and combinations thereof.

A8. The modified release tablet according to claim A7, wherein the modifying release agent is glyceryl dibehenate.

A9. The modified release tablet according to any one of A5 to A8, wherein the lubricant is selected is selected from the group consisting of magnesium stearate, calcium stearate, stearic acid, sodium stearyl fumarate, talc, and a combination thereof.

A10. The modified release tablet according to claim A9, wherein the lubricant is magnesium stearate.

A11. The modified release tablet according to any one of A5 to A10, wherein the glidant is selected from the group consisting of colloidal silicon dioxide, starch and talc and combination thereof.

A12. The modified release tablet according to A11, wherein the glidant is colloidal silicon dioxide.

A13. The modified release tablet according to any one of A5 to A12, wherein the additional pharmaceutically acceptable excipients are selected from pH adjusting agents and bulking agents.

A14. The modified release tablet according to any one of A5 to A13, wherein the enteric coating comprises an enteric polymer, a diluent, and optionally a plasticizer.

A15. The modified release tablet according to A14, wherein the enteric coating comprises an ethacrylic acid-ethyl acrylate copolymer (1:1) dispersion in water and propylene glycol.

A16. The modified release tablet according to A14, wherein the enteric coating comprises methacrylic acid-methacrylate copolymer (1:1) in an alcoholic solution with triethyl citrate.

A17. The modified release tablet according to any one of A5 to A16, wherein the core of the tablet comprises from 500 to 1500 mg of deferiprone.

A18. The modified release tablet according to A17, wherein the core of the tablet comprises 1000 mg of deferiprone.

A19. A process for the preparation of the modified release tablet according to any one of A5 to A18, said process comprising:
i) mixing deferiprone with the modifying release agent and the additional pharmaceutically acceptable excipients, if present to form a mixture;
ii) wet-granulating the mixture obtained in step (i) in a high shear granulator followed by drying and screening to produce a granulate;
iii) mixing the granulate obtained in step (ii) with the lubricant/glidant to form a mixture;
iv) compressing the mixture obtained in step (iii) to form a tablet; and
v) coating the tablet.

A20. A process for the preparation of the modified release tablet according to any one of A5 to A18, said process comprising:

i) mixing deferiprone with the modifying release agent and the additional pharmaceutically acceptable excipients, if present;
ii) adding the lubricant/glidant and further mixing to form a mixture;
iii) directly compressing the mixture obtained in step (ii) to form a tablet; and
iv) coating the tablet.

A21. A method of treating a disease which causes an overload of iron, comprising administering the pharmaceutical formulation of A1 or the modified release tablet of any one of A2 to A18.

A22. A method of treating and/or preventing a disease which is caused by an overload of iron, comprising administering the pharmaceutical formulation of A1 or the modified release tablet of any one of A2 to A18.

A23. The method of claim A21, wherein the disease is thalassemia or sickle cell anemia.

A24. The method of claim A21, wherein the iron overload is transfusional iron overload.

The invention claimed is:

1. A delayed release tablet comprising: (a) a core comprising about 1000 mg deferiprone, wherein the deferiprone is in an amount of about 85.0% to about 95.0% by weight of the tablet, a modifying release agent comprising glyceryl esters of long fatty acids in an amount of about 1.0% to about 2.0% by weight of the tablet, a lubricant and/or glidant in an amount of about 0 to about 2.0% by weight of the tablet, and additional pharmaceutically acceptable excipients in an amount of about 0 to 13.0% by weight of the tablet; and (b) an enteric coating; wherein the tablet is suitable for twice a day oral administration; and wherein the tablet releases less than about 20% of the deferiprone within 120 minutes when measured by USP Apparatus Type I basket method at 100 rpm in 900 mL at 37° C. and a pH of 1.2 and about 60% or more of the deferiprone within 180 minutes when measured by USP Apparatus Type I basket method at 100 rpm in 900 mL at 37° C. and a pH of 6.8.

2. The delayed release tablet according to claim 1, wherein the modifying release agent is selected from the group consisting of glyceryl palmitostearate, glyceryl monostearate, glyceryl dibehenate, and combinations thereof.

3. The delayed release tablet according to claim 2, wherein the modifying release agent is glyceryl dibehenate.

4. The delayed release tablet according to claim 1, wherein the lubricant is selected from the group consisting of magnesium stearate, calcium stearate, stearic acid, sodium stearyl fumarate, talc, and a combination thereof.

5. The delayed release tablet according to claim 4, wherein the lubricant is magnesium stearate.

6. The delayed release tablet according to claim 1, wherein the glidant is selected from the group consisting of colloidal silicon dioxide, starch and talc and combination thereof.

7. The delayed release tablet according to claim 6, wherein the glidant is colloidal silicon dioxide.

8. The delayed release tablet according to claim 1, wherein the additional pharmaceutically acceptable excipients are selected from pH adjusting agents and bulking agents.

9. The delayed release tablet according to claim 1, wherein the enteric coating comprises an enteric polymer, a diluent, and optionally a plasticizer.

10. The delayed release tablet according to claim 9, wherein the enteric coating comprises an ethacrylic acid-ethyl acrylate copolymer (1:1) dispersion in water and propylene glycol.

11. The delayed release tablet according to claim 9, wherein the enteric coating comprises methacrylic acid-methacrylate copolymer (1:1) in an alcoholic solution with triethyl citrate.

12. A process for the preparation of the delayed release tablet according to claim 1, said process comprising:
   i) mixing deferiprone with the modifying release agent and the additional pharmaceutically acceptable excipients, if present to form a mixture;
   ii) wet-granulating the mixture obtained in step (i) in a high shear granulator followed by drying and screening to produce a granulate;
   iii) mixing the granulate obtained in step (ii) with the lubricant and/or glidant to form a mixture;
   iv) compressing the mixture obtained in step (iii) to form a tablet; and
   v) coating the tablet.

13. A process for the preparation of the delayed release tablet according to claim 1, said process comprising:
   i) mixing deferiprone with the modifying release agent and the additional pharmaceutically acceptable excipients, if present;
   ii) adding the lubricant and/or glidant and further mixing to form a mixture;
   iii) directly compressing the mixture obtained in step (ii) to form a tablet; and
   iv) coating the tablet.

14. A method of treating a disease which causes an overload of iron, comprising administering the delayed release tablet of claim 1.

15. The method of claim 14, wherein the disease is thalassemia or sickle cell anemia.

16. The method of claim 14, wherein the iron overload is transfusional iron overload.

17. A method of treating and/or preventing a disease which is caused by an overload of iron, comprising administering the delayed release tablet of claim 1.

* * * * *